(12) United States Patent
Basile

(10) Patent No.: US 8,921,315 B1
(45) Date of Patent: Dec. 30, 2014

(54) METHOD OF INCREASING SURVIVAL OF A HUMAN SUBJECT HAVING EXPOSURE TO AN ACUTE EXPOSURE TO NON-THERAPEUTIC WHOLE BODY IONIZATION BY ADMINISTERING A THERAPEUTICALLY EFFECTIVE DOSE OF IL-12

(75) Inventor: Lena A. Basile, Tujunga, CA (US)

(73) Assignee: Neumedicines, Inc., Pasadena, CA (US)

( * ) Notice: Subject to any disclaimer, the term of this patent is extended or adjusted under 35 U.S.C. 154(b) by 193 days.

(21) Appl. No.: 12/430,016

(22) Filed: Apr. 24, 2009

Related U.S. Application Data

(60) Provisional application No. 61/125,508, filed on Apr. 24, 2008.

(51) Int. Cl.
*A61K 38/20* (2006.01)
*C07K 14/54* (2006.01)
*A61P 7/06* (2006.01)

(52) U.S. Cl.
USPC .............................. 514/7.9; 514/7.6; 424/85.2

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,674,841 A * | 10/1997 | Pragnell et al. | 514/12 |
| 5,744,132 A | 4/1998 | Warne et al. | |
| 2005/0136034 A1 * | 6/2005 | Chen et al. | 424/85.2 |
| 2007/0053832 A1 * | 3/2007 | Frincke et al. | 424/1.11 |

OTHER PUBLICATIONS

Schwartz et al; *Enhanced Hematopoietic Recovery in Irradiated Mice Pretreated with Interleukin-1*; Immunopharmacology and Immunotoxicoloty, 9 (2&3), 371-389 (1987).

Chen et al; *IL-12 Facilitates Both the Recovery of Endogenous Hematopoiesis and the Engraftment of Stem Cells after Ionizing Radiation*; Experimental Hematology 35, 203-213 (2007).

Hixon et al; *Administration of Either Anti-CD40 or Interleukin-12 following Lethal Total Body Irradiation Induces Acute Lethal Toxicity Affecting the Gut*; Biology of Blood and Marrow Transplantation; 8:316-325 (2002.

Neta et al; *Cytokines in Radioprotection. Comparison of the Radioprotective Effects of IL-1 to IL-2, GM-CSF and IFNγ*; Lymphokine Research, vol. 5, supp. 1, 105-110 (1986).

Neta et al; *Interleukin 1 is a Radioprotector*; Jour. of Immunology, vol. 136, No. 7 (1986).

Neta et al; *IL-12 Protects Bone Marrow from and Sensitizes Intestinal Tract to Ionizing Radiation*; Jour. of Immunology, 153: 4230 (1994).

Netal et al; *Modulation with Cytokines of Radiation Injury: Suggested Mechanisms of Action*; Environmental Health Perspectives; vol. 105, supp. 6; 1463-1465 (1997).

Leong et al., Optimized expression and specific activity of IL-12 by directed molecular evolution, Proc Nat Acad Sci USA., Feb. 4, 2003, 100(3):1163-1168.

Colombo, M. et al. "Interleukin-12 in Anti-tumor Immunity and Immunotherapy." Cytokine & Growth Factor Reviews 13 (2002), 155-168.

Hudis, C., et al. "Dose-Dense Chemotherapy in Breast Cancer and Lymphoma." Seminars in Oncology, vol. 31, No. 3, Suppl 8 (Jun. 2004), 19-26.

Ploemacher, R., et al. "Interleukin-12 Enhances Interleukin-3 Dependent Multilineage Hematopoietic Colony Formation Stimulated by Interleukin-11 or Steel Factor." Leukemia, vol. 7, No. 9 (Sep. 1993), 494 1374-1380.

Ploemacher, R., et al. "Interleukin-12 Syngerizes with Interleukin-3 and Steel Factor to Enhance Recovery of Murine Hemopoietic Stem Cells in Liquid Culture." Leukemia, vol. 7, No. 9 (Sep. 1993), 1381-1388.

Ryffel, B. "Interleukin-12: Role of Interferon-y in IL-12 Adverse Effects." Clinical Immunology and Immunopathology, vol. 83, No. 1, Apr. 1997, 18-20.

Office Action cited in related U.S. Appl. No. 13/353,179, dated Oct. 1, 2012.

* cited by examiner

*Primary Examiner* — Gyan Chandra
(74) *Attorney, Agent, or Firm* — Foley & Lardner LLP

(57) ABSTRACT

The present invention provides methods for increasing survival in a subject, and/or preserving bone marrow function, and/or promoting hematopoietic recovery or restoration. The methods include administering a dose of IL-12 to the subject following an acute exposure to non-therapeutic whole body ionizing radiation. Formulations and kits are also provided.

26 Claims, 15 Drawing Sheets

A

B

METHOD OF INCREASING SURVIVAL OF A HUMAN SUBJECT HAVING EXPOSURE TO AN ACUTE EXPOSURE TO NON-THERAPEUTIC WHOLE BODY IONIZATION BY ADMINISTERING A THERAPEUTICALLY EFFECTIVE DOSE OF IL-12

CROSS-REFERENCES TO RELATED APPLICATIONS

The present invention claims priority to U.S. Provisional Patent Application No. 61/125,508, filed Apr. 24, 2008, the teachings of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with US Government support under contract number BAA-BARDA-08-08 awarded by the Biomedical Advanced Research and Development Authority, within the Department of Health and Human Services. The US Government has certain rights in this invention.

BACKGROUND OF THE INVENTION

The hematological effects of acute, high dose total body irradiation (TBI) can lead to death without supportive care, such as hematopoietic transplant, transfusions and other supportive care measures. However, such supportive measures cannot be readily administered to a potentially large number of victims of high dose radiation exposure following a nuclear accident or direct acts of terrorism. If such disasters were to occur, military personnel and civilians alike would be left in great jeopardy. One of the deleterious effects of high dose radiation is the induction of a hematopoietic syndrome. To counteract the potentially lethal effects of hematopoietic syndrome, effective remedial drugs that can be quickly distributed shortly after the radiation incident are in great need.

Currently, there are no available drugs that are effective in increasing survival and regenerating hematopoiesis. Moreover, in the face of a radiation-related disaster or act of terrorism, the immediate distribution of such effective drugs to military personnel or civilians, if these were to be available, would not be practically possible. It is anticipated that a lag time of at least several hours, and perhaps 24 hours or longer, would be necessary to distribute such drugs to the scene of such a radiation disaster or act of terrorism. Thus, it is critically important that effective drugs that can be used to increase survival and regenerate hematopoiesis exhibit efficacy at protracted time intervals following acute exposure to ionizing radiation.

Several studies performed in the mid 80's suggested that proinflammatory cytokines could confer radioprotection when administered prior to lethal doses of radiation (Neta R. et al., Lymphokine Res. 1986;5 Suppl 1:S105-10; Neta R. et al., J Immunol. 1986 April 1;136(7):2483-5; Schwartz G. N. et al., Immunopharmacol Immunotoxicol. 1987;9(2-3):371-89). However, it was recognized by several later studies that the use of IL-12 for prophylactic and therapeutic treatments of lethal irradiation suffered from significant drawbacks. One such adverse effect was that IL-12 administered at a high dose of 1000 ng per mouse radiosensitized, rather than radioprotected, the gastrointestinal tract, resulting in lethal gastrointestinal syndrome in irradiated mice (Neta R. et al., J Immunol. 1994 November 1;153(9):4230-7). This work led to the conclusion that IL-12 sensitized the intestinal tract at levels necessary for protection of bone marrow cells (Neta R., Environ Health Perspect. 1997 December;105 Suppl 6:1463-5).

Consistent with these findings, Hixon et al. (Hixon et al., Biol Blood Marrow Transplant. 2002;8(6):316-25) showed that repeated administration of 500 ng IL-12 to BALBc mice who received bone marrow transplants following lethal whole body irradiation, resulted in acute lethal toxicity within 4 to 6 days. In contrast, Hixon et al. demonstrate that under identical conditions, BALBc mice that did not receive IL-12 administration recovered 100% of the time.

In the event of a nuclear event, whether accidental or malicious, pre-administration of drugs that promote survival is simply not possible. For example, in the event of a nuclear disaster, where large numbers of people and animals may require therapeutic administration, sufficient time will be required for the large-scale distribution of radiation treatments. Methods are needed for treatment that are effective when administered at protracted times following acute exposure to whole body ionizing radiation.

As such, there remains a need in the art for drugs that are effective in increasing survival and regenerating hematopoiesis when administrated at protracted times following acute exposure to whole body ionizing radiation. The present invention satisfies these and other needs by providing methods of treating a subject following an acute exposure to non-therapeutic whole body ionizing radiation via administration of IL-12 at protracted timepoints.

BRIEF SUMMARY OF THE INVENTION

The present invention relates to the use of Interleukin-12 (IL-12) for increasing survival and promoting hematopoietic recovery following acute exposure to non-therapeutic ionizing radiation. Use of the methods of the present invention will increase the number of survivors from a radiation-related disaster, such as a terrorist attack with a dirty bomb.

In one aspect, the present invention provides methods for increasing survival, and/or preserving bone marrow function, and/or promoting hematopoietic recovery or restoration in a subject following acute exposure to non-therapeutic, acute whole body ionizing radiation, comprising the administration of a therapeutically effective dose of IL-12.

In a related aspect, the present invention provides pharmaceutically acceptable formulations of IL-12 for increasing survival, and/or preserving bone marrow function, and/or promoting hematopoietic recovery or restoration in a subject following acute exposure to non-therapeutic whole body ionizing radiation.

In another aspect, the present invention provides kits useful for increasing survival, and/or preserving bone marrow function, and/or promoting hematopoietic recovery or restoration in a subject following acute exposure to non-therapeutic whole body ionizing radiation, comprising one or more therapeutically effective dose of IL-12.

Further aspects, objects, and advantages of the invention will become apparent upon consideration of the detailed description and figures that follow.

DETAILED DESCRIPTION OF THE INVENTION

I. Definitions

Figure 1:
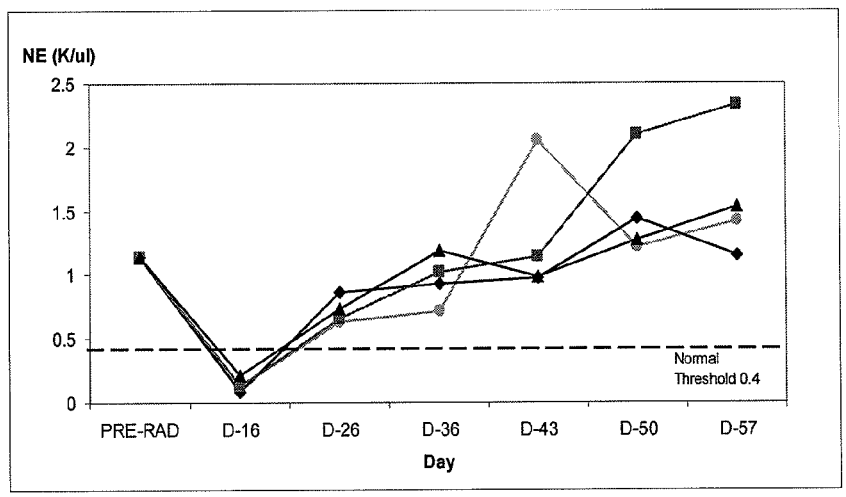
FIG. 1(A-C) shows that IL-12 facilitates multilineage hematopoietic recovery at various time points of administration and dosages, and even facilitates significant recovery of all blood groups at 3 hours post radiation (9 Gy). The blood recovery of neutrophils (1A), red blood cells (1B) and platelets (1C) are shown in the graph. The normal threshold count level is depicted for the different blood cell groups (dotted horizontal line). The depicted treatment groups are as follows: IL-12 (200 ng; 30 µg/m$^2$) administered 3 hrs after radiation (♦), IL-12 (100 ng; 15 µg/m$^2$) administered 24 hours before radiation (●), IL-12 administered 24 hours before and 2 hr after radiation (100 ng pre/50 ng post; 15 µg/m$^2$ pre/7.5 µg/m$^2$ post) (■), and IL-12 administered 24 hours before and 2 hr after radiation (100 ng pre/100 ng post; 15 µg/m$^2$ pre/185 µg/m$^2$ post) (▲). No control mice remained at 16 days post radiation for blood analysis. Bactrim was removed at 48 days.
Figure 1:
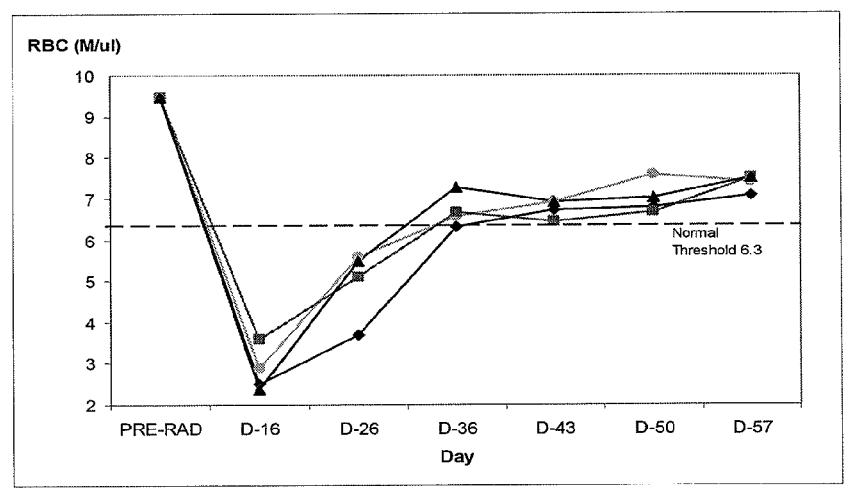
Figure 1:
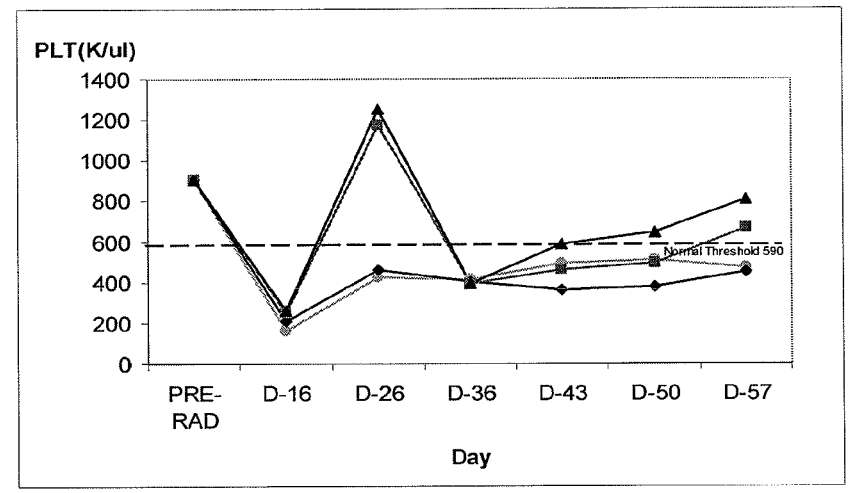

"Interleukin-12 (IL-12)" as used herein includes any recombinant IL-12 molecule that yields at least one of the properties disclosed herein, including native IL-12 molecules, variant IL-12 molecules and covalently modified IL-12 molecules, now known or to be developed in the future, produced in any manner known in the art now or to be developed in the future. Generally, the amino acid sequence of the IL-12 molecule used in embodiments of the invention is the canonical human sequence related to IL-12p70. IL-12 comprises two subunits, IL-12A (p35) and IL-12 B (p40) Polymorphisms, however, are known to exist for IL-12, especially in the p35 subunit. In particular, a known polymorphism can exist at amino acid 247 of the p35 human subunit, where methionine is replaced by threonine. Still other embodiments of the invention include IL-12 molecules where the native amino acid sequence of IL-12 is altered from the native sequence, but the IL-12 molecule functions to yield the properties of IL-12 that are disclosed herein. Alterations from the native, species-specific amino acid sequence of IL-12 include changes in the primary sequence of IL-12 and encompass deletions and additions to the primary amino acid sequence to yield variant IL-12 molecules. An example of a highly derivatized IL-12 molecule is the redesigned IL-12 molecule produced by Maxygen, Inc. (Leong SR, et al., Proc Natl Acad Sci U S A. 2003 February 4;100(3):1163-8.), where the variant IL-12 molecule is produced by a DNA shuffling method. Also included are modified IL-12 molecules included in the methods of invention, such as covalent modifications to the IL-12 molecule that increase its shelf life, half-life, potency, solubility, delivery, etc., additions of polyethylene glycol groups, polypropylene glycol, etc., in the manner set forth in U.S. Pat. Nos. 4,640,835; 4,496,689; 4,301,144; 4,670,417; 4,791,192 or 4,179,337, each of which is hereby incorporated by reference. One type of covalent modification of the IL-12 molecule is introduced into the molecule by reacting targeted amino acid residues of the IL-12 polypeptide with an organic derivatizing agent that is capable of reacting with selected side chains or the N- or C-terminal residues of the IL-12 polypeptide. Other IL-12 variants included in the present invention are those where the canonical sequence has been altered to increase the glycosylation pattern of the resultant IL-12 molecule, as compared with the native, non-altered IL-12. This method has been used to generate second generation molecules of erythropoietin, referred to as Aranesp. Both native sequence IL-12 and amino acid sequence variants of IL-12 may be covalently modified. Also as referred to herein, the IL-12 molecule can be produced by various methods known in the art, including recombinant methods. Since it is often difficult to predict in advance the characteristics of a variant IL-12 polypeptide, it will be appreciated that some screening of the recovered variant will be needed to select the optimal variant. A preferred method of assessing a change in the properties of variant IL-12 molecules is via the lethal irradiation rescue protocol disclosed below. Other potential modifications of protein or polypeptide properties such as redox or thermal stability, hydrophobicity, susceptibility to proteolytic degradation, or the tendency to aggregate with carriers or into multimers are assayed by methods well known in the art.

"Acute Radiation Syndrome" in humans as used herein includes an acute radiation exposure of 2Gy or greater.

"Hematopoietic Syndrome" as used herein includes damage to the bone marrow compartment which results in pancytopenia, i.e., a deficiency in peripheral blood cell counts for all blood cell types, namely white blood cells, red blood cells and platelets. Hematopoietic Syndrome also refers to loss of hematopoietic progenitor and stem cells in the bone marrow compartment.

"Survival" as used herein includes an increase in survival that can be measured in non-human species as compared to control groups, such as mice or non-human primates.

"Hematopoietic Recovery" as used herein includes early recovery of peripheral blood cell counts for white blood cells, red blood cells and platelets, as compared to control groups and as measured in non-human species, such as mice or non-human primates.

"Preservation of bone marrow function" as used herein includes early recovery of cellularity or colony forming units in the bone marrow compartment, or any other measure of bone marrow function, as compared to control groups and as measured in non-human species, such as mice and non-human primates.

A "therapeutically effective amount or dose" or "sufficient amount or dose" as used herein includes a dose that produces effects for which it is administered, for example, a dose sufficient for increasing survival, and/or preserving bone marrow function, and/or promoting hematopoietic recovery or restoration in a subject that has been exposed to an acute dose of whole body ionizing radiation. The exact dose will depend on the purpose of the treatment, the timing of the IL-12 administration, certain characteristics of the subject to be treated, the total amount or timing of irradiation, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

Generally, a dose of a therapeutic agent, according to the methods and compositions of the present invention, can be expressed in terms of the total amount of drug to be administered (i.e., ng, μg, or mg). Preferably, the dose can be expressed as a ratio of drug to be administered to weight or surface area of subject receiving the administration (i.e., ng/kg, μg/kg, ng/$m^2$, or μg/$m^2$). When referring to a dose in terms of the mass to be administered per mass of subject (i.e., ng/kg), it will be understood that doses are not equivalent between different animals, and thus conversion factors will need to be used to ensure that one animal receives the same dose equivalent as another animal. Suitable factors for the conversion of a mouse "dose equivalent" to a "dose equivalent" of a different animal are given in the look-up table below. Thus, in a preferred embodiment, doses are given in terms of mass to surface area (i.e., ng/$m^2$, or μg/$m^2$), which are equivalent for all animals. The following basic conversion factors can be used to convert ng/kg to ng/$m^2$: mouse=3.0, hamster=4.1, rat=6.0, guinea pig=7.7, human=38.0 (Cancer Chemother Repts 50(4):219(1966)).

TABLE 1

Conversion factors and equivalent doses for several animals.

| Species | Weight (kg) | Total Dose (ng) | Dose (ng/kg) | Dose (ng/$m^2$) | Conversion Factor |
|---|---|---|---|---|---|
| Human | 65 | 25655.82 | 394.7 | 15000 | 0.0794 |
| Mouse | 0.02 | 99.47 | 4973.44 | 15000 | 1.0000 |
| Hamster | 0.03 | 130.2 | 4339.87 | 15000 | 0.8726 |
| Rat | 0.15 | 381.12 | 2540.8 | 15000 | 0.5109 |
| Guinea Pig | 1.00 | 1335 | 1335 | 15000 | 0.2684 |
| Rabbit | 2 | 2381.1 | 1190.55 | 15000 | 0.2394 |
| Cat | 2.5 | 2956.44 | 1182.57 | 15000 | 0.2378 |
| Monkey | 3 | 3681.75 | 1227.25 | 15000 | 0.2468 |
| Dog | 8 | 6720 | 840 | 15000 | 0.1689 |

As used herein, the term "intermediate dose" includes doses between a range of about 15 μg/$m^2$ and about 75 μg/$m^2$, or between a range of about 20 μg/$m^2$ and about 75 μg/$m^2$, between a range of about 22.5 μg/$m^2$ and about 67.5 μg/$m^2$, between a range of about 22.5 μg/$m^2$ and about 52.5 μg/$m^2$, between a range of about 30 μg/$m^2$ and about 60 μg/$m^2$, between a range of about 37.5 μg/$m^2$ and about 52.5 μg/$m^2$, and all doses and ranges in-between.

As used herein, the term "low dose" includes doses less than about 15 μg/$m^2$, or less than about 14 μg/$m^2$, or less than about 13 μg/$m^2$, 12 μg/$m^2$, 11 μg/$m^2$, 10 μg/$m^2$, 9 μg/$m^2$, 8 μg/$m^2$, 7 μg/$m^2$, 6 μg/$m^2$, 5 μg/$m^2$, 4 μg/$m^2$, 3 μg/$m^2$, 2 μg/$m^2$, 1 μg/$m^2$, or less than about 900 ng/$m^2$, 800 ng/$m^2$, 700 ng/$m^2$, 600 ng/$m^2$, 500 ng/$m^2$, 400 ng/$m^2$, 300 ng/$m^2$, 200 ng/$m^2$, or 100 ng/$m^2$. In certain embodiments, a low dose includes an ultralow dose.

As used herein, the term "ultralow dose" includes doses less than about 3 μg/$m^2$, 2 μg/$m^2$, 1 μg/$m^2$, or less than about 900 ng/m², 800 ng/m², 700 ng/m², 600 ng/m², 500 ng/m², 400 ng/m², 300 ng/m², 200 ng/m², or 100 ng/m².

II. Embodiments

In one aspect, the present invention is based on the surprising discovery that Interleukin-12 (IL-12) increases the survival of subjects exposed to lethal and sub-lethal acute doses of non-therapeutic whole body ionizing radiation. Significantly, it was found that administration of IL-12 following acute doses of ionizing radiation resulted in the regeneration of hematopoietic activity and peripheral blood cell counts in lethally irradiated mice, yielding complete hematopoietic recovery without the use of transplanted cells.

Advantageously, it was found that IL-12 has the unique and remarkable property of being able to confer survival on lethally irradiated mammals when administered at protracted time points after radiation. Specifically, it was found that IL-12 can rescue about 90-100% of mammals when administered at 6 hours or 24 hours after radiation.

In one aspect, a single dose of IL-12 is sufficient to confer significant survival, bone marrow preservation, and promotion of hematopoietic recovery. In other aspects, IL-12 may be administered in more than one dose such as 2, 3, 4, 5 or more doses.

Accordingly, in one aspect, the present invention provides a method for increasing survival in a subject, and/or preserving bone marrow function, and/or promoting hematopoietic recovery or restoration comprising the administration of a dose of IL-12 to the subject following an acute exposure to non-therapeutic whole body ionizing radiation. In one embodiment, the dose of IL-12 is less than about 100 μg/m². In one embodiment, the dose of IL-12 is less than about 75 μg/m². In another embodiment, the low dose can be between about 1 μg/m² and about 100 μg/m², such as 1 μg/m², 5 μg/m², 10 μg/m², 15 μg/m², 20 μg/m², 25 μg/m², 30 μg/m², 35 μg/m², 40 μg/m², 45 μg/m², 50 μg/m², 55 μg/m², 60 μg/m², 65 μg/m², 70 μg/m², 75 μg/m², 80 μg/m², 85 μg/m², 90 μg/m², 95 μg/m² and 100 μg/m² and all doses in-between. In a particular embodiment, the preferred dose of IL-12 is less than about 75 μg/m². In one embodiment, the dose of IL-12 is either between a range from about 100 μg/m² to about 18 μg/m² or between a range from about 15 μg/m² to about 1 μg/m².

In certain embodiments, the IL-12 is a mammalian IL-12, recombinant mammalian IL-12, murine IL-12 (mIL-12), recombinant murine IL-12 (rmIL-12), human IL-12 (hIL-12), recombinant human IL-12 (rhIL-12), canine IL-12 or rIL-12, feline IL-12 or rIL-12, bovine IL-12 or rIL-12, equine IL-12 or rIL-12, or biologically active variants or fragments thereof. In one specific embodiment, the rhIL-12 is HemaMax™ (Neumedicines Inc.). In certain embodiments, the IL-12 can be modified in a fashion so as to reduce the immunogenicity of the protein after administration to a subject. Methods of reducing the immunogenicity of a protein are well known in the art and include, for example, modifying the protein with one or water soluble polymers, such as a PEG, a PEO, a carbohydrate, a polysialic acid, and the like.

In another aspect, the present invention provides methods for increasing survival in a subject, and/or preserving bone marrow function, and/or promoting hematopoietic recovery or restoration comprising the administration of an intermediate dose of IL-12 to the subject following an acute exposure to non-therapeutic whole body ionizing radiation. In one embodiment, the intermediate dose of IL-12 is between a range of about 15 μg/m² and about 100 μg/m², or between a range of about 20 μg/m² and about 75 μg/m², between a range of about 22.5 μg/m² and about 67.5 μg/m², between a range of about 22.5 μg/m² and about 52.5 μg/m², between a range of about 30 μg/m² and about 60 μg/m², between a range of about 37.5 μg/m² and about 52.5 μg/m², and all doses and ranges in-between. In a particular embodiment, the preferred intermediate dose of IL-12 is between a range of about 22.5 μg/m² and about 52.5 μg/m².

In another aspect, the present invention provides methods for increasing survival in a subject, and/or preserving bone marrow function, and/or promoting hematopoietic recovery or restoration comprising the administration of a low dose of IL-12 to the subject following an acute exposure to non-therapeutic whole body ionizing radiation. In one embodiment, the low dose of IL-12 is less than about 15 μg/m². In another embodiment, the low dose can be between about 3 μg/m² and about 12 μg/m², such as 3 μg/m², 4 μg/m², 5 μg/m², 6 μg/m², 7 μg/m², 8 μg/m², 9 μg/m², 10 μg/m², 11 μg/m², and 12 μg/m² and all doses in-between. In a particular embodiment, the preferred low dose of IL-12 is about 6 μg/m².

In one particular embodiment, a method is provided for increasing survival, and/or preserving bone marrow function, and/or promoting hematopoietic recovery or restoration in a human comprising the administration of a low dose of IL-12 to said human following an acute exposure to non-therapeutic whole body ionizing radiation. In a specific embodiment, the method for treating a human comprises administering a low dose of rhIL-12 in a range between about 1 hour and about 24 hours after acute exposure to whole body ionizing radiation, wherein the low dose is less than about 400 ng/kg (15 μg/m²).

In another aspect, the present invention provides methods for increasing survival in a subject, and/or preserving bone marrow function, and/or promoting hematopoietic recovery or restoration comprising the administration of an ultralow dose of IL-12 to the subject following an acute exposure to non-therapeutic whole body ionizing radiation. In one embodiment, an ultralow dose of IL-12 used, such as a dose of less than about 3 μg/m². In another embodiment, the ultralow dose may be between about 300 ng/m² and about 2400 ng/m², or between about 600 ng/m² and about 1200 ng/m². In a particular embodiment, the low dose of IL-12 is about 900 ng/m².

In still yet another aspect, the present invention provides a method for increasing survival, and/or preserving bone marrow function, and/or promoting hematopoietic recovery or restoration in a human comprising the administration of an ultralow dose of IL-12 to the subject following an acute exposure to non-therapeutic whole body ionizing radiation. In a specific embodiment, the method for treating a human comprises administering a low dose of rhIL-12 in a range between about 1 hour and about 24 hours after acute exposure to whole body ionizing radiation, wherein the low dose is less than about 80 ng/kg (3 μg/m²).

In certain embodiments of the invention, a low or ultralow dose of IL-12 suitable for administration may be less than about 14 μg/m², or less than about 13 μg/m², 12 μg/m², 11 μg/m², 10 μg/m², 9 μg/m², 8 μg/m², 7 μg/m², 6 μg/m², 5 μg/m², 4 μg/m², 3 μg/m², 2 μg/m², 1 μg/m², or less than about 900 ng/m², 800 ng/m², 700 ng/m², 600 ng/m², 500 ng/m², 400 ng/m², 300 ng/m², 200 ng/m², or 100 ng/m².

It is well known that solutions of proteins that are formulated at low concentrations are susceptible to loss of a significant fraction of the protein prior to administration. One major cause of this problem is adsorption of the protein on the sides of tubes, vials, syringes, and the like. Accordingly, in certain aspects, when administered at low or ultralow doses, it will be beneficial to administer IL-12 along with a suitable carrier molecule or bulking agent. In one embodiment, the carrier agent may be a protein suitable for pharmaceutical administration, such as albumin. Generally, the carrier molecule or protein will be present in the formulation in excess of IL-12 in order to minimize the amount of IL-12 lost prior to administration. In certain embodiments, the carrier will be present at a concentration of at least about 2 times the concentration of IL-12, or at a concentration of at least about 3, 4, 5, 6, 7, 8, 9, 10, 25, 50, 100, or more times the concentration of IL-12 in the formulation.

Generally the IL-12 doses used in the methods for increasing survival in a subject, and/or preserving bone marrow function, and/or promoting hematopoietic recovery or restoration in a subject following an acute exposure to non-therapeutic whole body ionizing radiation will be high enough to be effective for the treatment of a radiation syndrome, but low enough to mitigate negative side effects associated with IL-12 administrations, including for example, radiosensitivity of the GI tract and INF-γ up-regulation.

Advantageously, as provided by the methods of the present invention, administration of IL-12 may occur during any suitable time period following exposure to acute whole body radiation, up to and including about a week after exposure. Although the total dose of acute radiation will factor into the time period in which IL-12 should be administered, according to one embodiment, IL-12 may be administered at any time up to about 96 hours following exposure to radiation. In other embodiments, IL-12 can be administered at any time up to about 72 hours post-irradiation, or at a time up to about 60 hours, 48 hours, 36 hours, 24 hours, 18 hours, 12 hours, 8 hours, 6 hours, or less following exposure to radiation.

In one specific embodiment, IL-12 is administered to a subject in need thereof between a range of about 1 hour to about 72 hours after exposure to ionizing radiation. In another embodiment, IL-12 is administered between a range of about 1 hour and about 24 hours after exposure, or between a range of about 6 hours and about 24 hours following exposure to an acute dose of whole body ionizing radiation. Of great importance for the usefulness of IL-12 in the face of a radiation disaster is the fact that IL-12 can be administered at protracted time points following acute exposure to ionizing radiation. IL-12 is effective at any time point post radiation up to one week, but can provide especially high effectiveness at time points up to 96 hours post radiation.

In certain other aspects, IL-12 can be administered at any reasonable time point post radiation event, and be effective in increasing survival, and/or preserving bone marrow function, and/or promoting hematopoietic recovery. IL-12 administered at time points of up to 3 hours, 6 hours, 24 hours, 48 hours and 72 hours are efficacious in increasing survival, preserving bone marrow function, and promoting hematopoietic recovery. However, on one aspect, IL-12 acts on a residual subpopulation of hematopoietic stem cells, and thus it is expected to be effective at 96 hours, 120 hours and up to one week following acute exposure to ionizing radiation.

In another aspect of the invention, methods are provided for increasing survival in a subject, and/or preserving bone marrow function, and/or promoting hematopoietic recovery or restoration comprising the administration of more than one dose of IL-12 to a subject at protracted times following acute exposure to non-therapeutic whole body ionizing radiation. For example, in one embodiment, the method comprises the administration of a first therapeutically effective dose of IL-12 at a time up to about 24 hours post-irradiation and a second therapeutically effective dose of IL-12 at a second time up to about 72 hours after said first dose. In a particular embodiment, the first IL-12 dose can be administered between a range of about 1 hour and about 24 hours post-irradiation, or between a range of about 6 hours and about 24 hours post-irradiation, and said second IL-12 dose between a range of about 48 hours and about 1 week post-irradiation, or between a range of about 48 hours and about 94 hours post irradiation.

In one specific embodiment, the methods herein comprise administering a first dose of less than about 75 $\mu g/m^2$ IL-12 to a subject at a time between about 1 hour and about 24 hours after acute exposure to whole body radiation. In other embodiments, the method comprises administration of less than about 60 $\mu g/m^2$ IL-12, or less than about 45 $\mu g/m^2$ IL-12, 30 $\mu g/m^2$ IL-12, 15 $\mu g/m^2$ IL-12, or less IL-12 at an effective time after acute exposure to radiation.

In other embodiments, methods of multiple-dose IL-12 administration can comprise the administration of a first low or ultralow dose of IL-12, for example, a first dose of less than about 15 $\mu g/m^2$, or less than about 14 $\mu g/m^2$, or less than about 13 $\mu g/m^2$, 12 $\mu g/m^2$, 11 $\mu g/m^2$, 10 $\mu g/m^2$, 9 $\mu g/m^2$, 8 $\mu g/m^2$, 7 $\mu g/m^2$, 6 $\mu g/m^2$, 5 $\mu g/m^2$, 4 $\mu g/m^2$, 3 $\mu g/m^2$, 2 $\mu g/m^2$, 1 $\mu g/m^2$, or less than about 900 $ng/m^2$, 800 $ng/m^2$, 700 $ng/m^2$, 600 $ng/m^2$, 500 $ng/m^2$, 400 $ng/m^2$, 300 $ng/m^2$, 200 $ng/m^2$, or 100 $ng/m^2$.

When administered in multiple doses, i.e. two, three, four, or more, the first IL-12 dose and subsequent IL-12 dose(s) can be equivalent doses, or they can be different dose amounts. For example, in certain embodiments, subsequent dose(s) can be administered at about 90% of the initial dose, or at about 80%, 75%, 70%, 60%, 50%, 40%, 30%, 25%, 20%, 10% or less of the original dose.

In one particular embodiment, a method is provided for increasing survival in a human, and/or preserving bone marrow function, and/or promoting hematopoietic recovery or restoration, said method comprising the steps of administering a first dose of IL-12 to said human within about 24 hours following an acute exposure to non-therapeutic whole body ionizing radiation, wherein said first dose is less than about 100 $\mu g/m^2$ and subsequently administering a second dose of IL-12 to said human within about 96 hours following said acute exposure to non-therapeutic whole body ionizing radiation, wherein said second dose is less than about 100 $\mu g/m^2$. In a specific embodiment, said second dose is administered at least about 24 hours after said first dose is administered. In another specific embodiment, said second dose is less than said first dose.

In yet other embodiments, methods are provided for increasing survival in a subject, and/or preserving bone marrow function, and/or promoting hematopoietic recovery or restoration following an acute exposure to non-therapeutic whole body ionizing radiation, comprising repeated administration of IL-12 for at least about a week, or at least about 2 weeks, or at least about 3, 4, 5, 6, 7, 8, 9, 10, 11, 12, or more weeks. In certain embodiments, the doses may be administered about once every 12 hours, or about once every 24 hours, or about 1, 2, 3, 4, 5, 6, or seven times a week. In other embodiments, IL-12 may be administered about every other week or about 1, 2, 3, 4, 5, or more times a month. In some embodiments, each IL-12 doses may be less than about 100 $\mu g/m^2$, or alternatively be an intermediate dose, a low dose, or an ultra low dose. In yet other embodiments, the doses may be decreased during the course of a repeated administration.

Without being held to any particular theory, it is believed that when the hematopoietic system is compromised, as with acute whole body radiation, the IL-12 mediated pathway leading to the production of INF-γ may be sensitized. Consistent with this, Hixon et al. observed that when IL-12 is administered to mice following whole body irradiation and bone marrow transplant, INF-γ levels are greatly increased and acute lethal toxicity of the gut results from the elevated levels of INF-γ. The observed acute lethal toxicity of the gut was dependant on INF-γ, as INF-γ knockout mice were resistant to IL-12 mediated toxicity. The experiments performed by Hixon et al. support a model in which IL-12 administration results in an increase of INF-γ levels, and therefore an increase in Crg-2 and Mig cytokine levels, resulting in anti-angiogenesis effects. Alternatively, but not mutually exclusive with the above, by performing bone marrow transplants prior to IL-12 administration, Hixon et al. provided INF-γ producing lymphocytes to the mice, further increasing the potential for INF-γ production.

Thus, a possible mechanism for the decreased hematopoietic side effects associated with certain embodiments of the invention is that when a relatively low dose IL-12 is given to a mammal whose hematopoietic system is compromised, the dose is insufficient to upregulate INF-γ production. Since INF-γ inhibits hematopoiesis and also appears to be the major cytokine responsible for toxicity, the absence of INF-γ upregulation upon administration of low and ultralow doses of IL-12, as used in the methods of the present invention, may be one of the factors underlying the discovery by the inventors that administration of low and ultralow doses of IL-12 provides a hematopoietic protective and recovery effect without apparent toxicity.

Also of significance is the demonstration that exogenous administration of IL-12 can expand long-term repopulating (LTR) hematopoietic stem cells (HSC) in vivo. Thus, without being bound by theory, HSC expansion by exogenous IL-12 can be the mechanism responsible for survival from hematopoietic injury resulting from lethal radiation exposure at later time points, e.g., 24 hours post-irradiation. Another potential mechanism relates to the ability of IL-12 to induce DNA repair and reduce apoptosis in hematopoietic stem cells (HSC) following radiation exposure.

While most bone marrow progenitor and stem cells are susceptible to cell death after high dose radiation, subpopulations of HSC or accessory cells are selectively more radioresistant, presumably because these cells exist in a largely noncycling ($G_0$) state. In humans, these radioresistant cells can play an important role in recovery of hematopoiesis after exposure to doses as high as 6 Gy, albeit with a reduced capacity for self-renewal in the absence of exogenous IL-12.

Another determinant for hematopoietic reconstitution is non-homogeneity of the radiation dose, which can spare some marrow sites that then become the foci of hematopoietic activity. In either case, i.e., either the residual presence of radioresistant HSC or inhomogeneity of the radiation dose, the present findings indicate that a subpopulation of HSC marked by the presence of the IL-12 receptor (IL-12R+) survives and persists after high dose radiation, and moreover, that this IL-12R+ HSC subpopulation is activated, expanded, and/or induced to repair itself upon exogenous administration of IL-12.

Following radiation exposure, it has been discovered that IL-12 is effective in mitigating the hematopoietic syndrome associated with acute radiation syndrome. Specifically, embodiments of the present invention provide methods for increasing survival, and/or preserving bone marrow function, and/or promoting hematopoietic recovery by administering one or more effective dose(s) of IL-12 to a subject following acute exposure to ionizing radiation.

For humans, as shown in Table 2, the early signs of hematopoietic syndrome start to occur in the range of radiation doses of 2 Gy or greater. Similarly, at radiation doses between about 5.5-7.5 Gy, pancytopenia and moderate GI damage occurs in humans. Advantageously, when administered according to the methods of the present invention, IL-12 is effective in alleviating the pancytopenia at these radiation dose levels, preserving bone marrow function and will not induce further GI damage. However, the radiation dose rate can also affect the relative level of radiation injury. Thus, two radiation doses given at two different dose rates can show differences in the severity of the relative radiation injury.

TABLE 2

Phases of Radiation Injury*

| Dose Range Gy | Prodrome | Manifestation of Illness | Prognosis (without Therapy) |
|---|---|---|---|
| 0.5-1.0 | Mild | Slight decrease in blood cell counts | Almost certain survival |
| 1.0-2.0 | Mild to moderate | Early signs of bone marrow damage | Highly probable survival (>90% of victims) |
| 2.0-3.5 | Moderate | Moderate to severe bone marrow damage | Probable survival |
| 3.5-5.5 | Severe | Severe bone marrow damage, slight GI damage | Death within 3.5-6 wk (50% of victims) |
| 5.5-7.5 | Severe | Pancytopenia and moderate GI damage | Death probable within 2-3 wk |
| 7.5-10.0 | Severe | Marked GI and bone marrow damage, hypotension | Death probable within 1-2.5 wk |
| 10.0-20.0 | Severe | Severe GI damage, pneuomonitis, altered mental status, cognitive dysfunction | Death certain within 5-12 d |
| 20.0-30.0 | Severe | Cerebrovascular collapse, fever, shock | Death certain within 2-5 d |

*Modified from Walker RI, Cerveny RJ, eds. (21), GI = gastrointestinal

For other mammals embraced by the methods and compositions of the present invention, for example mice, rats, guinea pigs, hamsters, cats, dogs, cattle, horses, sheep, pigs, rabbits, deer, monkeys, and the like, the radiation dose that can induce hematopoietic syndrome varies with the species and strain. For example, for rhesus monkeys, the $LD_{50}$ is about 7 Gy. For certain strains of mice, the $LD_{50}$ is also about 7 Gy, for example Balb-c mice. For other strains of mice, such as C57BL6, the $LD_{50}$ is about 7.5Gy. The $LD_{50}$ can also exhibit differences based on gender or general health status of the animal.

Although it would be difficult to determine the exact extent of radiation injury in a mammal exposed to acute ionizing radiation following a radiation-related disaster, IL-12, when used in accordance with embodiments of the present invention, will increase survival, and/or preserve bone marrow function, and/or promote hematopoietic recovery of peripheral blood cell counts.

Accordingly, in some embodiments of the present invention, IL-12 is administered to a subject that has been exposed to an acute dose of ionizing radiation of at least about 1.0 Gy, or an amount equivalent to an $LD_{10}$ in humans. In another embodiment, IL-12 is administered to a subject that has been exposed to about 3.5 Gy of ionizing radiation, or a dose equivalent to about $LD_{50}$ in humans. In yet other embodiments, IL-12 is useful for increasing survival, and/or preserving bone marrow function, and/or promoting hematopoietic recovery of peripheral blood cell counts in a subject exposed to at least about 2.0 Gy, or at least about 3.0 Gy, 4.0 Gy, 5.0 Gy, 6.0 Gy, 7.0 Gy, 8.0 Gy, 9.0 Gy, 10.0 Gy, 11.0 Gy, 12.0 Gy, 13.0 Gy, 14.0 Gy, 15.0 Gy, 20.0 Gy, 25.0 Gy, 30.0 Gy, or higher doses of acute ionizing radiation. Similarly, the dose of ionizing radiation can be expressed in terms of the percent lethal dose, for example, a dose equivalent of about $LD_1$, $LD_5$, $LD_{10}$, $LD_{20}$, $LD_{30}$, $LD_{40}$, $LD_{50}$, $LD_{60}$, $LD_{70}$, $LD_{80}$, $LD_{90}$, $LD_{95}$, $LD_{99}$, or $LD_{100}$.

A. Supportive Care

In another aspect of the invention, methods are provided for increasing survival in a subject, and/or preserving bone marrow function, and/or promoting hematopoietic recovery or restoration comprising the administration of one or more dose of IL-12 to a subject at protracted times following acute exposure to non-therapeutic whole body ionizing radiation, wherein supportive care is given to said subject simultaneously or following administration of IL-12.

Supportive care modalities useful in conjunction with IL-12 for treatment of a subject who has been exposed to an acute dose of whole body ionizing radiation include, without limitation, administration of fluids, one or more antibiotic, blood or blood component transfusions, administration of one or more growth factors or hematopoietic growth factors, combination therapies and the like.

In one embodiment, supportive care comprises the administration of one or more antibiotics. Antibiotic support can be any antibiotic that is useful in preventing infections during periods of low blood cell counts including, without limitation, bactrim, ciprofloxacin, moxifloxacin, and the like. Those of skill in the art will know of other antibiotics useful for supportive care.

In another embodiment, supportive care comprises administration of one or more growth factors, including hematopoietic growth factors. Many suitable hematopoietic growth factors are known in the art including, without limitation, colony stimulating factors (CSF, G-CSF, GM-CSF, M-CSF, IL-3), erythropoietin, IL-1, IL-4, IL-5, IL-6, IL-7, IL-11, and the like. Several FDA-approved hematopoietic growth factors are currently available, and thus may be used in the methods provided herein, such as G-CSF (Neupogen or Neulasta), IL-11, and erythropoietin (Epogen, Procrit or Aranesp). In some embodiments, supportive care comprises the administration of keratinocyte growth factor (KGF or FGF7).

In one particular embodiment, erythropoietin administration can increase survival up to about 50% over and above that of IL-12 alone when super-lethal doses are used with no other supportive care measures, such as antibiotic support or fluid administration. Super-lethal doses are defined herein as radiation doses at or above 5.5Gy. Erythropoietin is available as a FDA-approved recombinant protein drug for human use, such as Epogen, Procrit or Aranesp. Generally, dosing with these erythropoietin drugs will be simultaneous with or following the administration of IL-12. Erythropoietin drugs can be repeated as needed, but generally not administered more than every other day, or every third day. Preferably erythropoietin is administered about 48 hours after the last dose of IL-12.

An effective dose of erythropoietin for a human can be about 20 mg/kg, however, lower doses and higher doses are also effective in increasing survival when use as an adjuvant to IL-12 administration. Accordingly, in certain embodiments, erythropoietin is administered at about 1 mg/kg, or at about 2 mg/kg, 3 mg/kg, 4 mg/kg, 5 mg/kg, 10 mg/kg, 15 mg/kg, 20 mg/kg, 25 mg/kg, 30 mg/kg, 40 mg/kg, 50 mg/kg, or more for treatment in a human, or at a dose equivalent amount for treatment in an animal other than a human.

In another embodiment, supportive care comprises the administration of a blood transfusion. As used herein, a blood transfusion may encompass a whole blood transfusion, or alternatively, transfusion of a blood fraction or blood component, for example, a red blood cell transfusion, a platelet transfusion, a white blood cell transfusion. In a related embodiment, supportive care may comprise the administration of a bone marrow or bone marrow stem cell transplant.

B. Formulations

IL-12 composition provided herein and used according to the methods of the invention can be formulated for administration via any known method, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Further, an efficacious dose of IL-12 may differ with different routes of administration.

In certain embodiment IL-12 is administered following radiation exposure by intramuscular (IM) or subcutaneous (SC) routes. Advantageously, these modes of administration can be self-administered or administered by a person with little or no medical training. As such, this aspect of the invention allows for rapid responses under disaster conditions where attention by those medical staff may be limited. Other modes of administration, however, such as intravenous and intraperitoneal, are also compatible with the present invention.

The IL-12 compositions can be administered in a variety of unit dosage forms depending upon the method of administration. For example, unit dosage forms suitable for oral administration include, but are not limited to, powder, tablets, pills, capsules and lozenges. It is recognized that constructs when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

In some embodiments, the formulations provided herein further comprise one or more pharmaceutically acceptable excipients, carriers, and/or diluents. In addition, the formulations provided herein may further comprise other medicinal agents, carriers, adjuvants, diluents, tissue permeation enhancers, solubilizers, and the like. Methods for preparing compositions and formulations for pharmaceutical administration are known to those skilled in the art (see, for example, REMINGTON'S PHARMACEUTICAL SCIENCES, 18TH ED., Mack Publishing Co., Easton, Pa. (1990)). Formulations used according to the methods of the invention may include, for example, those taught in U.S. Pat. No. 5,744,132, which is hereby incorporated by reference in its entirety for all purposes.

C. Kits

In another aspect of the invention, kits are provided for increasing survival in a subject, and/or preserving bone marrow function, and/or promoting hematopoietic recovery or restoration following non-therapeutic acute exposure to whole body ionizing radiation. In one embodiment, a kit of the invention comprises one or more formulations of a therapeutically effective amount of IL-12. In certain embodiments, the therapeutically effective amount of IL-12 comprises a low dose of IL-12, for example, a dose that is less than about 15 $\mu g/m^2$. In other embodiments, the therapeutically effective amount of IL-12 may comprise an ultralow dose of IL-12, for example, a dose that is less than about 3 $\mu g/m^2$. In yet other embodiments, a kit as provided herein may comprise multiple doses or formulations suitable for multi-dose administration of IL-12 following radiation exposure.

In one specific embodiment, a kit is provided for increasing survival in a human, and/or preserving bone marrow function, and/or promoting hematopoietic recovery or restoration following non-therapeutic acute exposure to whole body ionizing radiation, comprising a low dose or ultralow dose of human IL-12. In one embodiment, the human IL-12 is recombinant IL-12 or a recombinant IL-12 variant. In the kits of the invention, IL-12 can be formulated so as to be delivered to a patient using a wide variety of routes or modes of administration. In a particular embodiment, IL-12 is formulated for injection in solution or as a lyophilized powder that can be easily reconstituted using sterile water or a physiologically acceptable buffer.

In some embodiments, the kits of the invention may also comprise a formulation of a compound useful for supportive care of IL-12 treatment following radiation exposure. Suitable compounds include, without limitation, antibiotics, for example, bactrim, ciprofloxacin, or moxifloxacin, and hematopoietic growth factors, such as CSF, G-CSF, GM-CSF,. M-CSF, IL-3, erythropoietin, erythropoietin-like molecules, IL-1, IL-4, IL-5, IL-6, IL-7, IL-11, and the like.

In certain embodiments, kits are provided for treating one or more animal following acute exposure to whole body ionizing radiation. For example, kits are provided for treating one or more of a human, dog, cat, guinea pig, hamster, cattle, horse, sheep, pig, rabbit, and the like. In a particular embodiment, these kits contain one or more dose of IL-12 specific for the animal to be treated. For example, a kit for treating cattle may comprise bovine IL-12, or a kit for treating horses may comprise equine IL-12. In other embodiments, the kits comprise, for example, murine or human IL-12 at a dose suitable for administration to the particular animal to be treated.

In certain aspects, the kits provided herein are optionally housed in a radiation proof container (e.g., lead) or alternatively, the container for the kit is radiation resistant or proof (e.g., lead).

III. EXAMPLES

Example 1

The IL-12-facilitated Survival as a Function of Administration Schedule Following Super-lethal Radiation (9 Gy)

This example illustrates the effects of administration time point of IL-12 in a comparative experiment, where various time points were directly compared to assess relative survival and hematopoietic recovery. IL-12 was administered at 3 hours after, 24 hours before, or 24 hours before and 2 hours after (at two different doses of IL-12) using a 9Gy radiation dose (unfractionated dose at a dose rate of 0.9 Gy/min (γ-ray from cesium 137 irradiator). In this example, female C57BL/6 mice were used (13 weeks of age). All injections were intravenous, and mice were started on antibiotics (Bactrim) following radiation.

As shown in Table 3, survival data demonstrate that there was not significant differences among the various time points evaluated. In fact, administration of IL-12 at 3 hours after radiation or 24 hours before radiation showed only a slight difference in survival, albeit the two groups were administered a different dose of IL-12. However, it was determined that 100 ng (15 µg/m$^2$) is the optimal dose of IL-12 when given 24 hours before lethal radiation. (See Table 3). Moreover, at the same overall dose of IL-12 (200 ng/mouse; 30 µg/m$^2$) given either in a split dose of given at 24 hour before and 2 hours after radiation or as a single dose given at 3 hours after radiation, there was no difference in relative survival. These data suggest that a residual subpopulation of hematopoietic stem cells persist after radiation that can be acted upon by IL-12.

TABLE 3

Survival as a Function of Time of Administration of IL-12 at an Acute Radiation Dose of 9 Gy

| Time of Administration | Dose of IL-12 | % Survival |
|---|---|---|
| PBS control | 0 | 0 |
| 3 hours after radiation | 200 ng (30 µg/m$^2$) | 60 |
| 24 hour before radiation | 100 ng (15 µg/m$^2$) | 50 |
| 24 hr before and 2 hr after | 100 ng, 50 ng (15 µg/m$^2$, 7.5 µg/m$^2$) | 70 |
| 24 hr before and 2 hr after | 100 ng, 100 ng (15 µg/m$^2$, 15 µg/m$^2$) | 60 |

Example 2.

The IL-12-facilitated Hematopoietic Recovery as a Function of Administration Schedule Following Super-lethal Radiation (9Gy)

The peripheral blood recovery for mice that survived the super-lethal radiation dose is shown in FIG. 1. Although there are some notable difference in the neutrophil and red blood cell recovery, overall the recovery of these two blood cell groups was quite similar, and did not vary significantly as a function of the time point of IL-12 administration. Platelet recovery, however, was significantly different for the 3 hour post- and 24 hour pre-radiation administration of IL-12, as compared to the split dose (pre-post) administration. For this example, mice were administered Bactrim in their drinking water, which is known to induce thrombocytopenia. Mice were taken off antibiotics at about 48 days, and subsequently, all groups showed an increase in platelet counts. There results show that IL-12 can facilitate recovery of all blood cell groups, including potent recovery of platelet counts, at super-lethal radiation dose (9Gy TBI). Also notable is the length of the survival time. Mice were monitored for 57 days and were terminated on day 60. All mice appeared in good health and had regained any losses in body weight.

Example 3

IL-12-facilitated Survival: Administration of IL-12 at 6 Hours After Lethal Radiation ($LD_{100/10}$) to Female Mice Without Antibiotic Support In this example, the effect of IL-12 when administered at 6 hours after an unfractionated (acute), lethal dose of radiation (8 Gy) without the addition of antibiotic support was evaluated.

Figure 2:
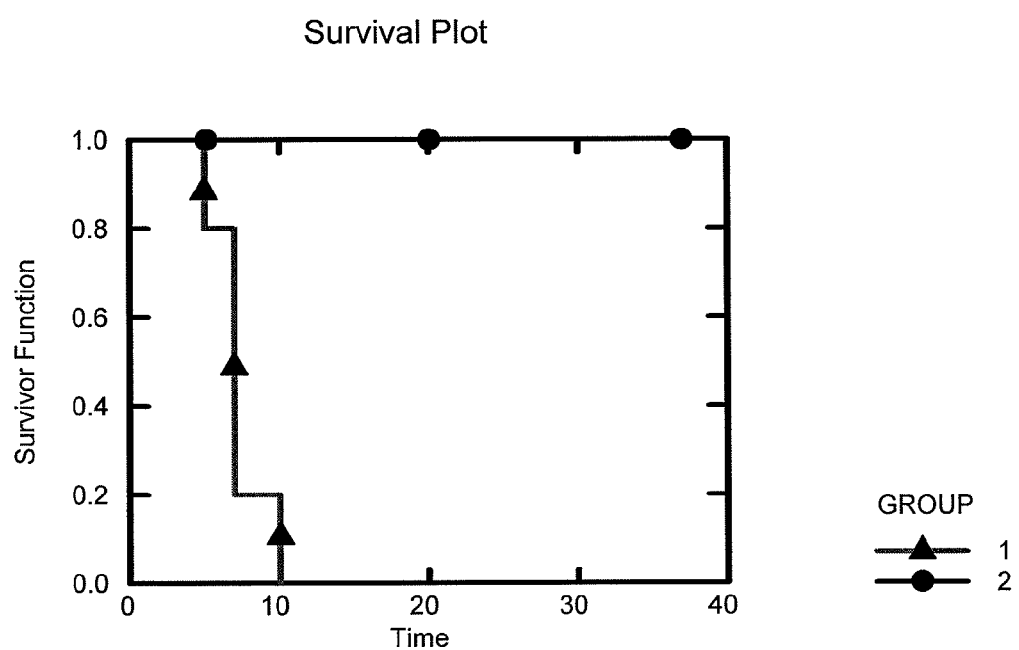
FIG. 2 shows survival effects of IL-12 when administered at 6 hours after a lethal dose of radiation ($LD_{100/10}$) and subcutaneous injection. Female mice C57BL/6 (9 weeks) were used for this experiment (5-6 mice per group).

A Kaplan-Meier plot of the data is shown in FIG. 2. Remarkably, at the $LD_{100/10}$, 100% of the IL-12-treated mice at 6 hour post radiation survived. Moreover, the health status of the IL-12-treated mice was remarkably stable during the period in which control mice experienced the effects of hematopoietic syndrome.

Figure 3:
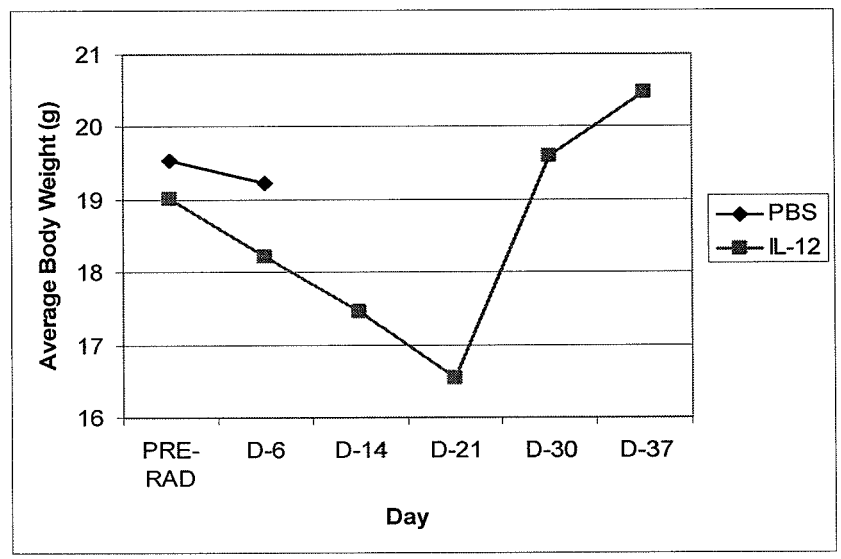
FIG. 3 shows the results of one aspect of the invention as a Kaplan-Meier plot. Group 1 received vehicle (phosphate buffered saline (PBS)) and Group 2 received an initial dose of IL-12 (120 ng; 18 µg/m$^2$) at 6 hours after radiation, followed by one subsequent dose of IL-12 (100 ng; 15 µg/m$^2$ at 3 days post radiation). No antibiotic support was administered. The radiation dose was 8Gy (0.9Gy/min); P=0.001 via Mantel Chi-square analysis. Mice did not receive antibiotic support.

As shown in FIG. 3, although the IL-12-treated mice did lose about 14%, on average of their body weight by day 21 post radiation, they had regained all of their lost body weight, and were slightly higher in weight than they were at the start of the experiment, by about day 30 (19.1 g on day 0 vs. 19.6 g on day 30).

As would be expected, statistical analyses revealed that the survival effect was highly significant via the Mantel Chi-Square statistical method (p=0.001), despite the small number of mice (n=5 for Group 1 and n=6 for Group 2). This example demonstrates the remarkable survival effects of IL-12 at 6 hours post radiation.

Example 4

IL-12-facilitated Survival: Administration of IL-12 at 6 Hours After Lethal Radiation ($LD_{100/21}$) Using Male Mice and No Antibiotic Support This example evaluated the effect of IL-12 when administered at 6 hours after an unfractionated (acute), lethal dose of radiation (8 Gy) in male mice without the addition of antibiotic support. This example shows a lethal radiation survival study using male mice.

Two groups of mice were first exposed to a 7 Gy dose of radiation and either treated with IL-12 or vehicle (PBS) at about 9 weeks of age. For the first round of radiation, Group 1 received PBS and Group 2 received IL-12, all mice survived following radiation. After 5 weeks, when it was clear that all mice were healthy enough to undergo a second round of radiation, the same mice were then subjected to a radiation dose of 8 Gy. At this point, the mice were about 14 weeks of age and weighed 27 grams on average. The IL-12 was adjusted according to the weight of the mice. For the second round of radiation, Group 1 again received only PBS and Group 3 also received PBS, and Group 2 received IL-12 again.

Figure 4:
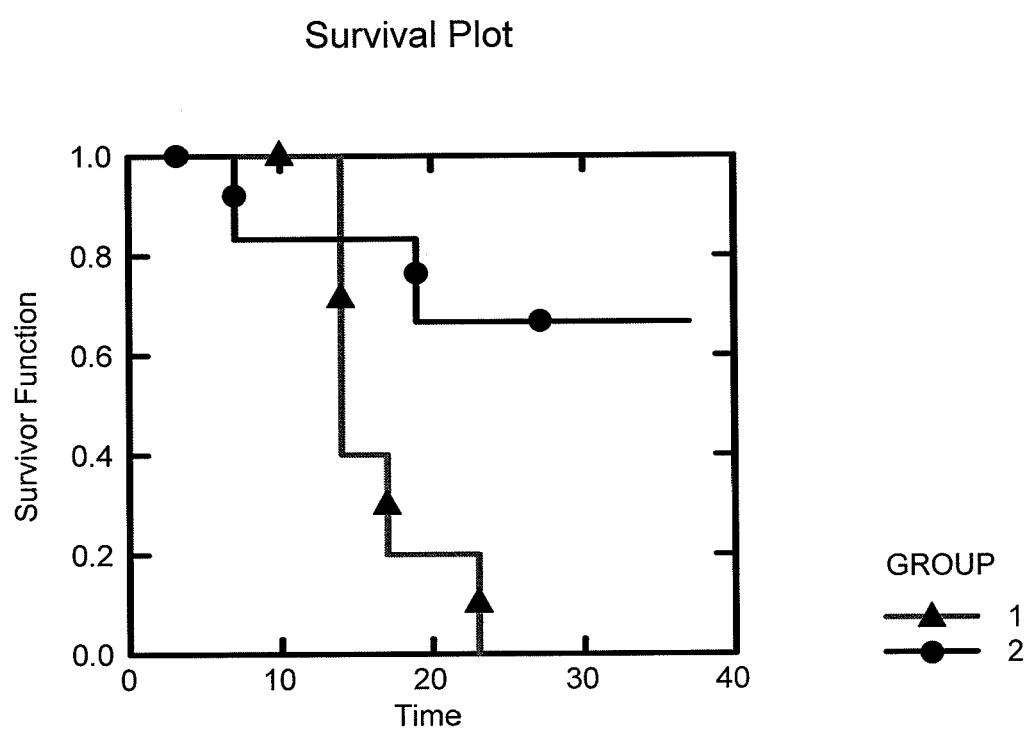
FIG. 4 shows remarkable survival effects when administered at 6 hours after a lethal dose of radiation ($LD_{100/21}$) and subcutaneous injection in male mice. C57BL/6 (14 weeks) were used for this experiment (5-6 mice per group). Mice were first exposed to a non-lethal dose of radiation at 7Gy. At 6 hours after radiation, mice were either treated with PBS (Group 1) or IL-12 (Group 2 (150 ng; 22.5 µg/m$^2$). All mice survived the 7Gy dose of radiation. On the next round of radiation, all mice received an 8 Gy radiation dose (0.9 Gy/min). On the second round of radiation, Group 3 received PBS and Group 2 again received the same dose of IL-12 (150 ng; 22.5 µg/m$^2$) that was administered in the first round of radiation, followed by a subsequent dose (100 ng; 15 µg/m$^2$) 48 hrs after the initial dose at 6 hr post radiation.
Figure 5:
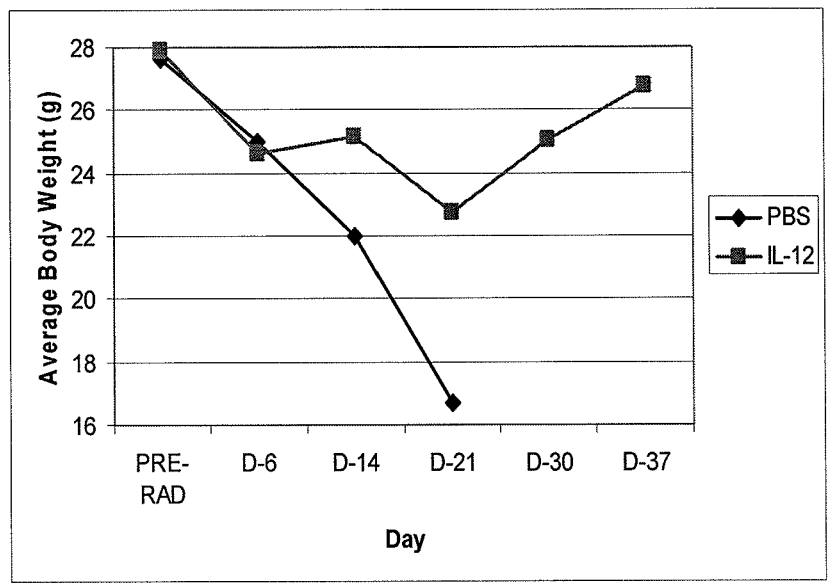
FIG. 5 shows a Kaplan-Meier plot from the second round of radiation. No antibiotic support was administered; P<0.05 via Mantel Chi-square analysis.
Figure 6:
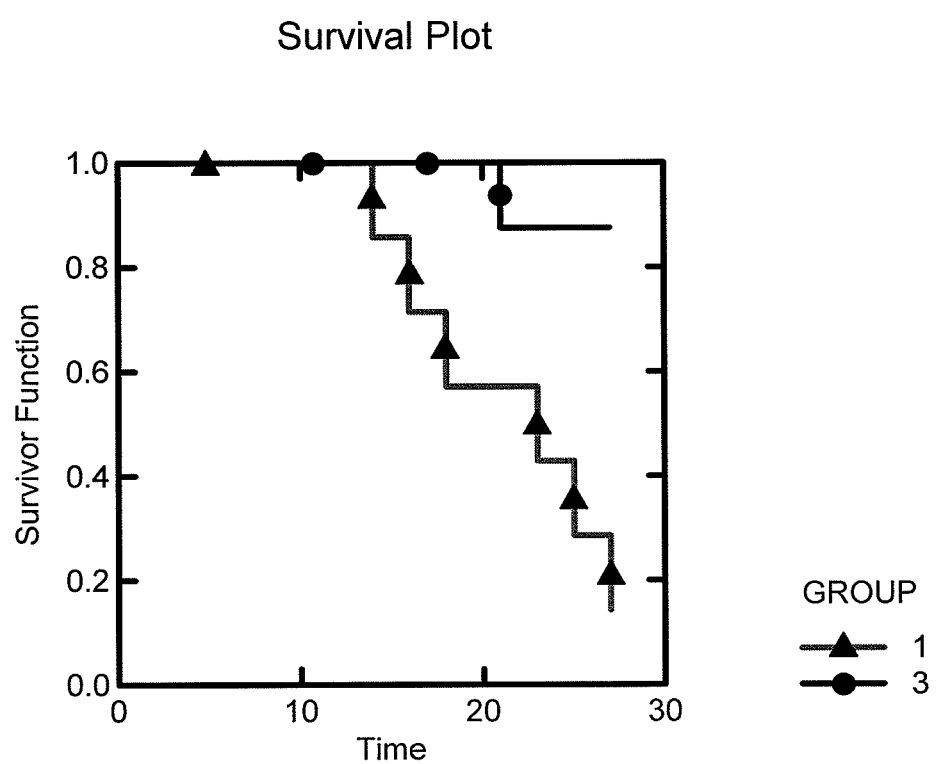
FIG. 6 shows survival effects as a result of IL-12 administration at 24 hours after a lethal dose of radiation ($LD_{90/27}$) and subcutaneous injection. Female mice C57BL/6 (9 weeks) were used for this experiment (7-8 mice per group). Group 1 received vehicle (phosphate buffered saline (PBS)) and Group 2 received an initial dose of IL-12 (120 ng; 18 µg/m$^2$) at 24 hours after radiation, followed by one subsequent dose of IL-12 (100 ng; 15 µg/m$^2$ at 3 days post radiation). No antibiotic support was administered. The radiation dose was 8 Gy (0.9 Gy/min); P=0.001 via Mantel Chi-square analysis.

A Kaplan-Meier plot of the data is shown in FIG. 4 (Groups 1 (PBS) vs. 2 (IL-12)). Remarkably, it was found that after receiving an accumulated dose of 15 Gy, nearly 70% of the IL-12-treated mice survived (Group 2) when IL-12 was administered at 6 hours post radiation. Moreover, the health status of the IL-12-treated mice in Group 2 was observed to be good during the entire observation period for the surviving mice. During the second round of radiation, surviving mice lost about 24% of their body weight by day 21 post radiation, and on day 30 these mice had regained 10% of their body weight. These results are shown in FIG. 6. Remarkably, statistical analyses revealed that the survival effect was significant via the Chi-Square statistical Mantel method ($p<0.05$), despite the small number of mice (n=5 for Group 1 and n=6 for Group 2).

The data presented in FIGS. 3 and 4 were collected at the same time, i.e., the mice were all irradiated at the same time and received the same radiation dose. However, there is clearly a notable difference in the survival curve for control female mice as compared to control male mice. This may be due to apparent differences in intrinsic radiation rescue response for males and females, such as sex differences in endogenous IL-12 production following radiation or other related factors.

Example 5

IL-12-facilitated Survival: Administration of IL-12 at 24 Hours After Lethal Radiation ($LD_{90/30}$) Using Female Mice and No Antibiotic Support In this example, IL-12 administration was evaluated when administered at 24 hours after an unfractionated (acute), lethal dose of radiation (8 Gy) without the addition of antibiotic support.

A Kaplan-Meier plot of the data is shown in FIG. 6. Remarkably, when IL-12 was administered at 24 hours after an 8 Gy radiation dose, 90% of the IL-12 treated mice survived, whereas only 14% of the control mice were alive at 27 days post radiation. Moreover, the health status of the IL-12-treated mice was remarkably stable during the period in which control mice experienced the effects of hematopoietic syndrome.

Figure 7:
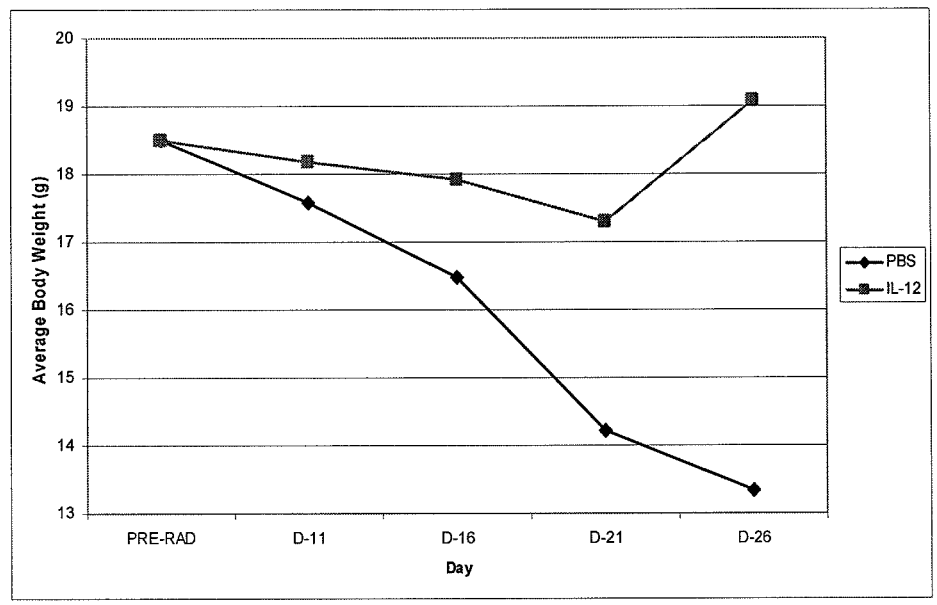
FIG. 7 shows a Kaplan-Meier plot at 27 days in the experimental timeline. No antibiotic support was used. P=0.005 via Mantel Chi-square analysis.

As shown in FIG. 7, although the IL-12-treated mice did lose about 10%, on average, of their body weight by day 21 post radiation, they had regained all of their lost body weight, and were slightly higher in weight than they were at the start of the experiment, by about day 27 (18.5 g on day 0 vs. 19.2 g on day 27).

Statistical analyses revealed that the survival effect was significant via the Mantel Chi-Square statistical method (p=0.001), despite the small number of mice (n=7 for Group 1 and n=8 for Group 2). This example demonstrates the remarkable survival effects of IL-12 at 24 hours post radiation.

Example 6

Low Dose Administration of IL-12 at 24 Hours and at 24 Hours and 72 Hours After a Lethal Dose of Acute Whole Body Irradiation ($LD_{80}$)

160 female C57BL/6 mice in 16 groups with 10 mice per group were irradiated with a lethal dose of acute whole body irradiation ($LD_{80/30}$) and then treated with IL-12 administration. Both the dose of IL-12 and the frequency of the dose (single vs. double dose) were investigated. In the double dose experiment, the first dose of IL-12 was administered at 24 hours post radiation and the second dose of IL-12 was administered at 72 hours post radiation. For the single dose experiment, IL-12 was administered at 24 hours post radiation only. An outline of the study is shown in Table 4.

TABLE 4

Experimental design for single dose and double dose IL-12 administration after acute whole body irradiation.

| Group | muIL-12 dose (ng per mouse) | muIL-12 dose ($\mu g/m^2$) |
|---|---|---|
| 4A: Double Dose Experiment* | | |
| 1 | 0 (vehicle) | 0 |
| 2 | 40 | 6 |
| 3 | 80 | 12 |
| 4 | 120 | 18 |
| 5 | 150 | 22.5 |
| 6 | 200 | 30 |
| 7 | 300 | 45 |
| 8 | 500 | 75 |
| 4B: Single Dose Experiment* | | |
| 1 | 0 (vehicle) | 0 |
| 2 | 40 | 6 |
| 3 | 80 | 12 |
| 4 | 120 | 18 |
| 5 | 150 | 22.5 |
| 6 | 200 | 30 |
| 7 | 300 | 45 |
| 8 | 500 | 75 |

*All injections were subcutaneous.

Figure 8:
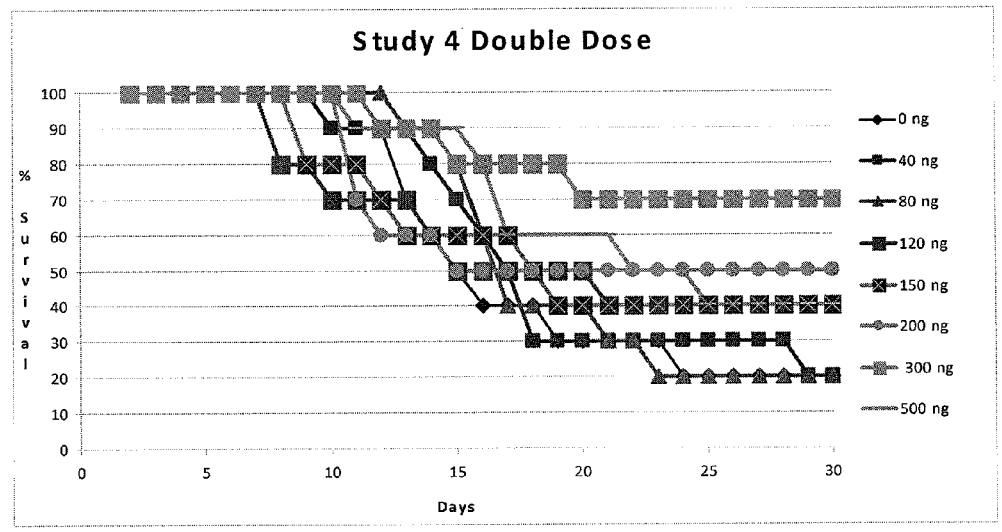
FIG. 8(A-B) shows the results of female C57BL/6 mice (10 per group), which were irradiated with an $LD_{80}$ dose of acute irradiation. The mice were then administered the indicated amounts of IL-12 as either (A) a double dose at 24 hours and 72 hours post irradiation, or (B) a single dose at 24 hour post irradiation. The survival rates for each of the groups are shown.
Figure 8:
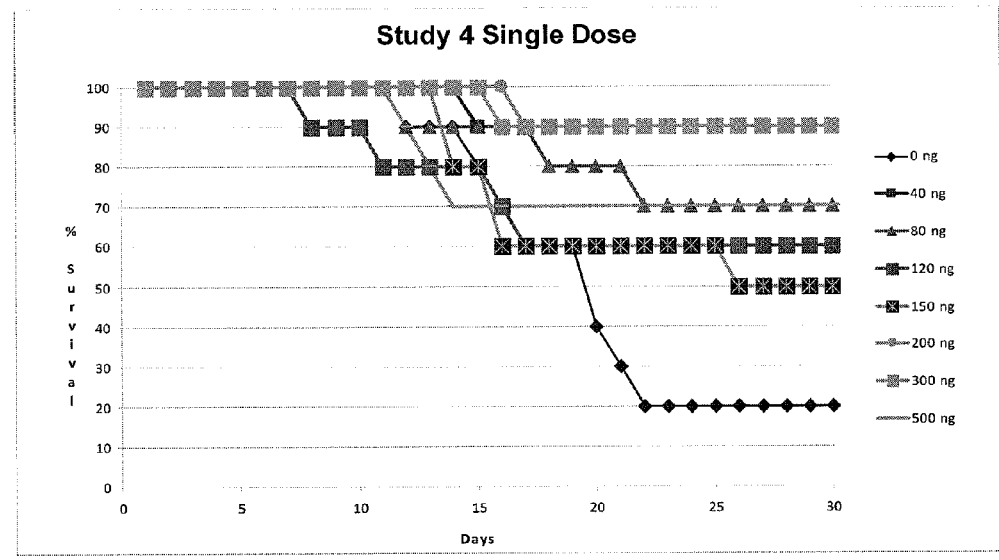
Figure 9:
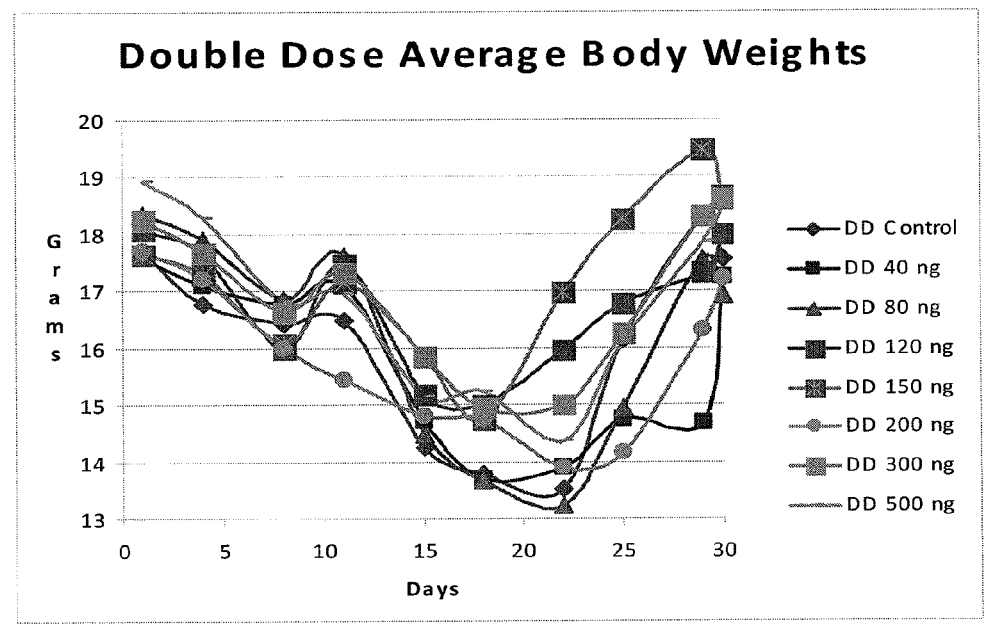
FIG. 9 shows the results of female C57BL/6 mice (10 per group), which were irradiated with an $LD_{80}$ dose of acute irradiation. The mice were then administered the indicated amounts of IL-12 as either (A) a double dose at 24 hours and 72 hours post irradiation, or (B) a single dose at 24 hour post irradiation. The average weight of the surviving mice are plotted as a function of time in days.
Figure 9:
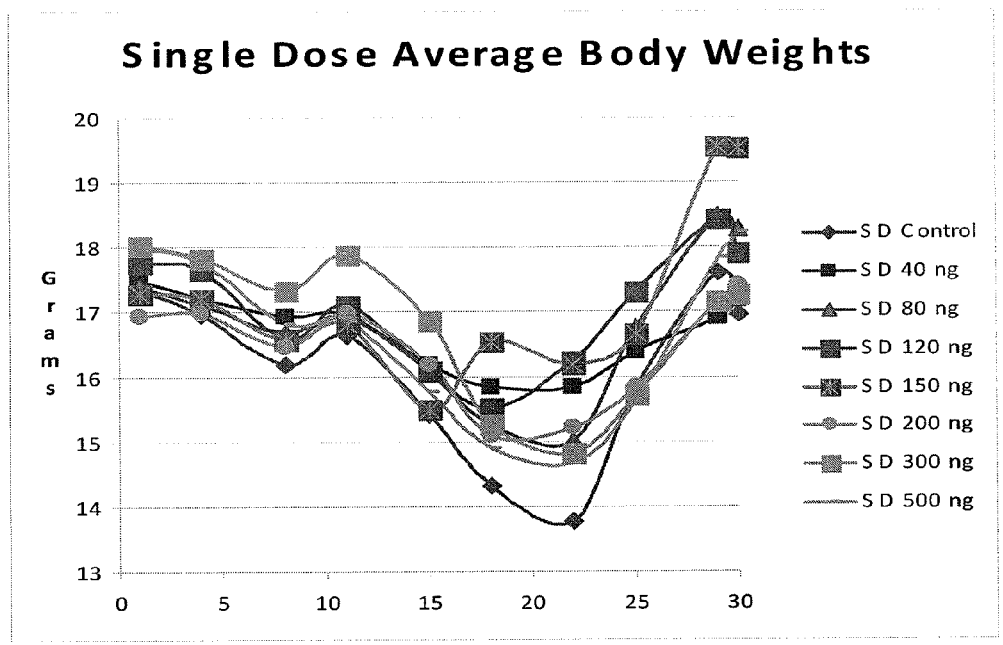

Mice treated with a double dose of IL-12 showed a linear dose response related to administration of muIL-12 at lethal radiation doses 24 and 72 hours post radiation (FIG. 8A), whereas studies of single dose treatments demonstrate a biphasic dose response related to administration of muIL-12 at lethal radiation doses 24 hours post radiation (FIG. 8B). For the double dose experiment, higher doses of muIL-12 gave better efficacy, as measured by survival following a $LD_{80}$ radiation dose with the most efficacious dose being 300 ng (45 μg/m$^2$) given twice. Interestingly, for the single dose experiments, the dose response curve was biphasic with 40 ng (6 μg/m$^2$) and 200-300 ng (30 μg/m$^2$-45 μg/m$^2$)) showing high efficacy at the same LD$_{80/30}$ radiation dose. Average body weights for the surviving mice are shown in FIG. 9.

The efficacy at 300 ng (45 μg/m$^2$) in the double dose experiment was 70% at the LD$_{80/30}$ radiation dose (FIG. 8A). Notably, in the double dose experiment, there were early deaths in many of the IL-12 treated groups, as compared to the control. Without being bound by theory, these early deaths may be due to protein aggregation resulting in immunogenicity. Consistent with this notion, there were very few early deaths in the single dose experiment. As can be seen via the statistical evaluation below, in the double dose experiment it appears that there may be two effects: 1) a highly therapeutic effect and 2) an effect that diminishes the efficacy of the therapeutic effect.

The results of the single dose experiments show that a single low dose of IL-12 (40 ng; 6 μg/m$^2$) administered at 24 hours after acute whole body irradiation resulted in 90% survival at the LD$_{80/30}$ (FIG. 8B). This single dose gave a 70% increase in survival as compared to the control. Moreover, this increase in survival was highly statistically significant (p<0.001; see statistical evaluation below).

Figure 14:
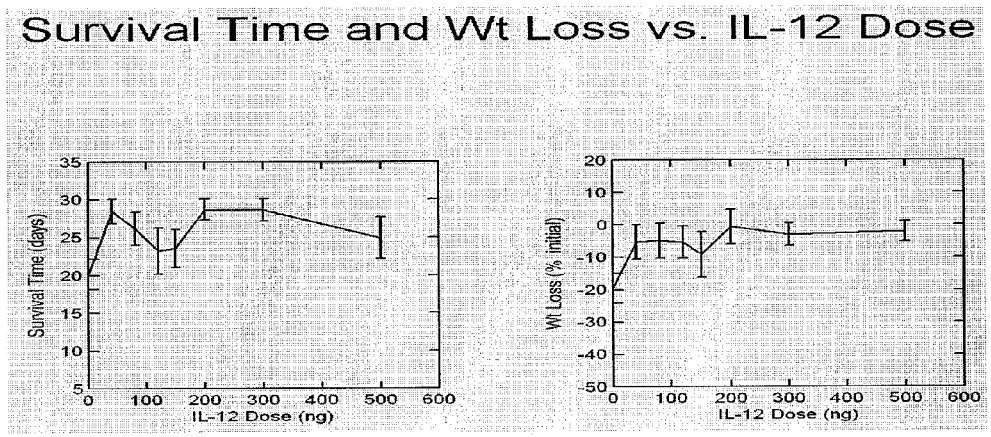
FIG. 14 illustrates a dose response curves for single dose administration of IL-12 24 hours after irradiation. Female C57BL/6 mice irradiated with an $LD_{80}$ dose of acute irradiation followed by administration of IL-12 at 24 hours post irradiation, as in example 6. Survival time and percent weight loss are plotted as a function of administered IL-12 dose.

For single dose experiments, The dose response curve was biphasic with a sharp increase in survival at 40 ng (6 μg/m$^2$), a dip in survival at intermediate doses and a second increase in survival time at doses exceeding 200 ng (30 μg/m$^2$; FIG. 14). Notably, weight loss was a highly significant predictor of lethality. Mice losing 20% or more of body weight did indeed subsequently die.

Without being bound by theory, the biphasic nature of the dose response curve (FIG. 14) may be explained by the presence of protein aggregates in the administered IL-12. It is possible that at the 40 ng (6 μg/m$^2$) dose, the least amount of aggregation is occurring, whereas in the middle of the dose range the protein is more aggregated, and in the higher dose range the protein is delivered as both an aggregated and non-aggregated form. Consistently, if there are more aggregates leading to some immunogenicity in the middle of the dose range, this might explain presence of a few early deaths, as compared to the control, in the middle dose range. This type of aggregation and the resultant biphasic dose response curve has been seen with other biologics.

Finally, it should be noted that the concentration actually delivered to the mice in this example may be as low as 10-20% of what is indicated. This may be caused by the loss of IL-12 protein due to adsorption on the sides of tubes and syringes used in the study, as is common with solutions of very low protein concentrations. These effects may be mitigated by various measures, including without limitation, the use of containers with reduced affinity for the non-specific protein interactions, or the pre-treatment of containers to reduce adsorption, as well as with the use of carrier molecules or proteins.

Statistical Analysis

Figure 10:
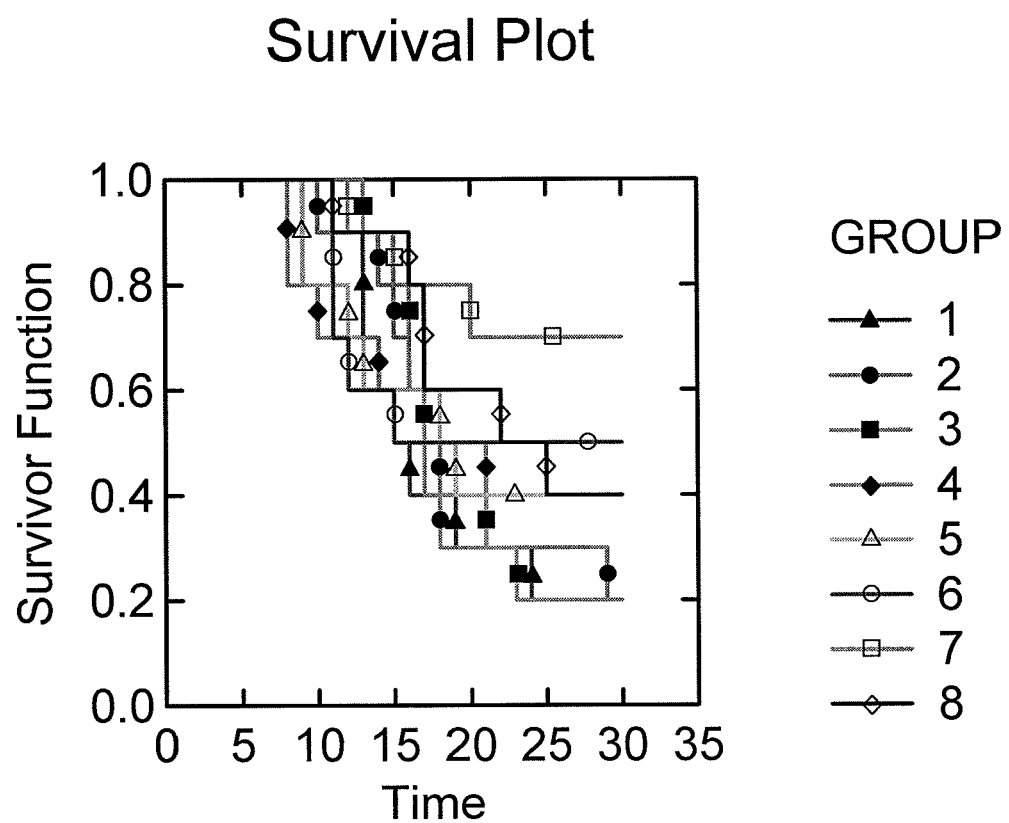
FIG. 10 illustrates a stratified K-M plot for double dose experiments performed with female C57BL/6 mice (10 per group). Briefly, the mice were irradiated with an $LD_{80}$ dose of acute irradiation followed by administration of a double dose of IL-12, as described in example 6, at 24 and 72 hours post irradiation. Survival analysis did not indicate a significant overall effect of IL-12 dose on survival (p<0.59; Tarone-Ware test).
Figure 11:
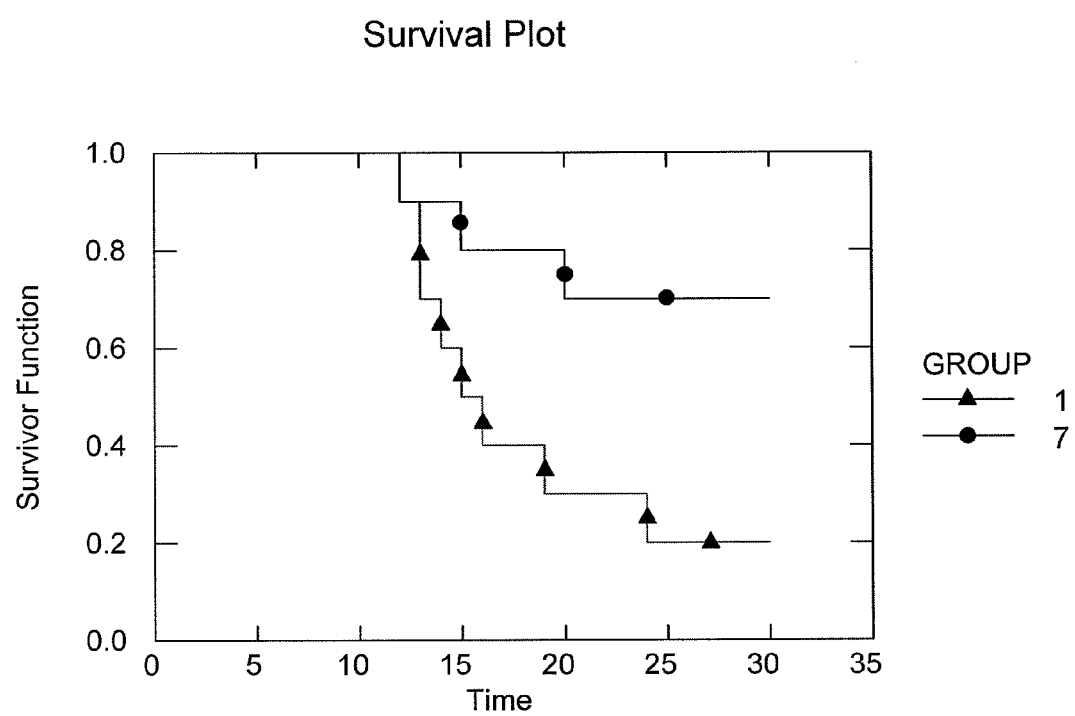
FIG. 11 illustrates a K-M plot of survival for group 1 (0 ng IL-12, vehicle control; (▲)) and group 7 (300 ng IL-12; 45 µg/m$^2$; (●)) female C57BL/6 mice irradiated with an $LD_{80}$ dose of acute irradiation followed by administration of IL-12 at 24 and 72 hours post irradiation. Survival analysis reveals that administration of 300 ng (45 µg/m$^2$) IL-12 at both 24 and 72 hours post irradiation resulted in a significant increase in survival (p<0.03; Tarone-Ware and Mantel-Cox tests).

FIG. 10 shows a stratified K-M analysis of the double dose experiments. In the double dosing experiments, doses of IL-12, 200-300 ng and above, increased survival in this experiment. Notably, when group 7 (300 ng; 45 μg/m$^2$) is compared to group 1 (0 ng, vehicle control), the effect was statistically significant (p<0.03; Tarone-Ware and Mantel methods; FIG. 11). In contrast to the single dose experiments, significant low dose therapeutic effects were not observed in the double dosing regimes. Weight loss was not a significant covariate in this experiment (FIG. 9A), suggesting that the double dose protocol allowed for considerable weight loss without death, particularly at the highest IL-12 dose.

Figure 12:
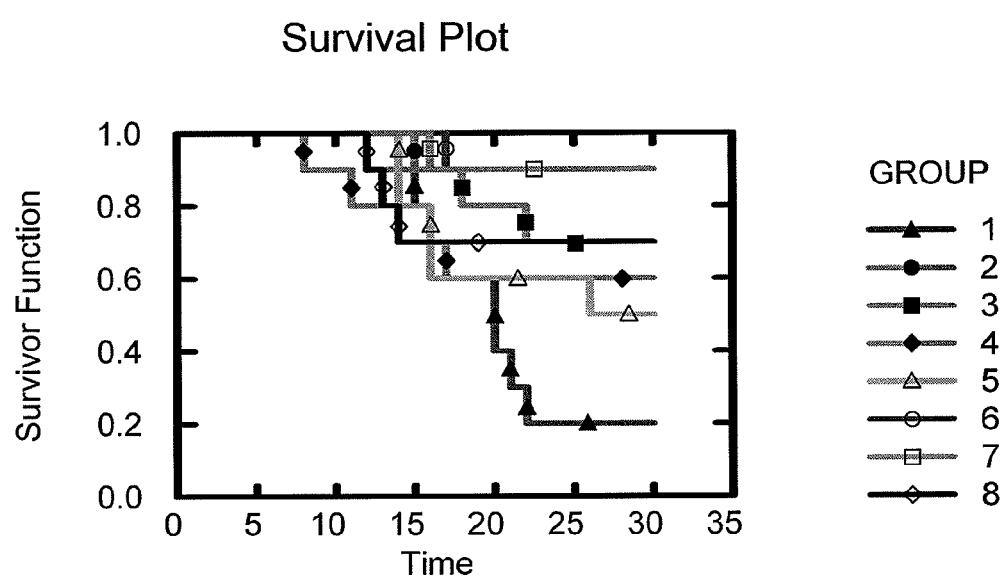
FIG. 12 illustrates a stratified K-M plot for single dose experiments performed with female C57BL/6 mice (10 per group). Briefly, the mice were irradiated with an $LD_{80}$ dose of acute irradiation followed by administration of a single dose of IL-12, as described in example 6, at 24 hours post irradiation. Survival analysis indicates a significant overall effect of IL-12 dose on survival (p<0.02; Tarone-Ware test).
Figure 13:
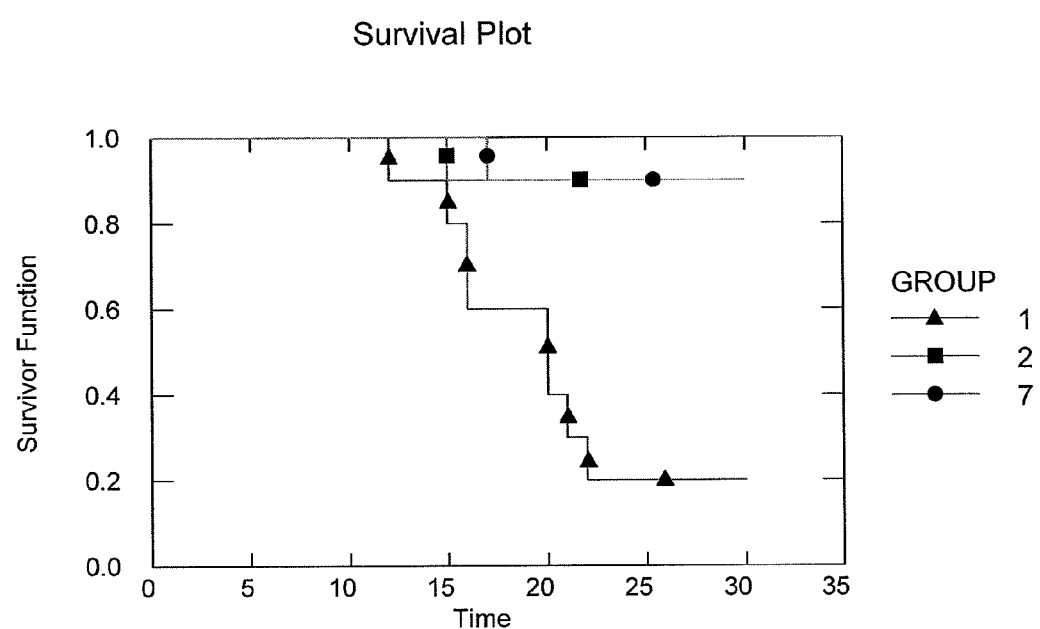
FIG. 13 illustrates a K-M plot of survival for group 1 (0 ng IL-12, vehicle control; (▲)), group 2 (40 ng IL-12; 6 µg/m$^2$ (■)), and group 7 (300 ng IL-12; 45 µg/m$^2$ (●)) female C57BL/6 mice irradiated with an $LD_{80}$ dose of acute irradiation followed by administration of IL-12 at 24 hours post irradiation. Survival analysis reveals that administration of 40 ng (6 µg/m$^2$) and 300 ng (45 µg/m$^2$) IL-12 at 24 hours post irradiation resulted in a significant increase in survival (p<0.001; Tarone-Ware test).

Stratified K-M analysis of the results generated in the single dose experiments indicated an overall statistically significant effect of IL-12 dose on survival time (p<0.02; Tarone-Ware method; FIG. 12). Strikingly, when groups 2 (40 ng; 6 μg/m$^2$) and 6 (200 ng; 30 μg/m$^2$) are compared with group 1 (0 ng, vehicle control) in a three way K-M analysis, the results are highly statistically significant (p<0.001; Tarone-Ware Method; FIG. 13).

Example 7

Determination of LD Values for Acute Whole Body Irradiation of C57BL/6 Female Mice Six groups of 10 female C57BL/6 mice each were subjected to increasing doses of total body radiation using a Gammacell 40 irradiator with Cesium source. The Specific dosage activity (Adjusted Dose Rate) for the irradiator was 5159 rad/hour. Groups were irradiated for the time periods shown in Table 5 in order to achieve the final dose of radiation as delineated in the table.

TABLE 5

Experimental design for acute exposure to whole body irradiation.

| Time (min:sec) | Total Body Dose (Rad) |
|---|---|
| 9:00 | 773.85 |
| 9:20 | 802.22 |
| 9:40 | 831.45 |
| 10:00 | 859.83 |
| 10:20 | 888.21 |
| 10:40 | 917.44 |

Figure 15:
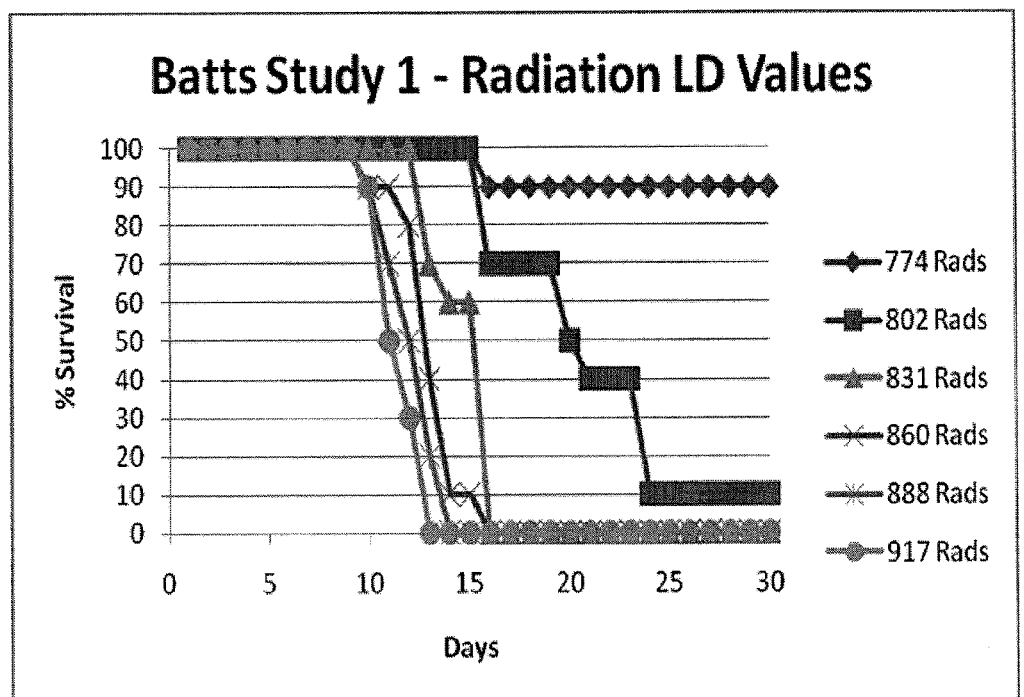
FIG. 15 illustrates a survival curve for female C57BL/6 mice irradiated with various acute doses of ionizing radiation.

The irradiated mice were housed for 30 days following irradiation. The mice were monitored daily for survival with the day of death recorded for each mouse. The Kaplan-Meier graph of the results is presented in FIG. 15. Calculated radiation exposures for LD$_{30(30)}$, LD$_{50(30)}$, and LD$_{70(30)}$ were about 782 rad (7.82 Gy), 788 rad (7.88 Gy), and 794 rad (7.94 Gy), respectively.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating a human subject, said method comprising:
   administering subcutaneously or intramuscularly at least one therapeutically effective dose of IL-12 to said subject at least about 24 hours following an acute exposure to non-therapeutic whole body ionizing radiation, wherein said dose increases the probability of survival of a subject by at least 10% over that observed with a subject who has not been administered IL-12 and exposed to the same level of radiation.

2. The method of claim 1, wherein said dose of IL-12 is less than about 100 μg/m2, less than about 75 μg/m2, less than about 15 μg/m2, less than about 12 μg/m2, or less than about 6 μg/m2.

3. The method of claim 1, wherein said acute exposure to whole body ionizing radiation is the result of a nuclear event.

4. The method of claim 1, wherein said acute exposure is at least about 3.5 Gy (LD50).

5. The method of claim 1, wherein said IL-12 is administered between a range of about 24 hours to about 72 hours after said acute radiation exposure.

6. The method of claim 5, wherein the IL-12 is administered at about 24 hours after said acute radiation exposure.

7. The method of claim 1, wherein supportive care is given to said subject simultaneously or following the administration of IL-12.

8. The method of claim 7, wherein supportive care comprises the administration of one or more antibiotics.

9. The method of claim 7, wherein supportive care comprises administration of one or more hematopoietic growth factors.

10. The method of claim 7, wherein supportive care comprises the administration of a blood transfusion.

11. The method of claim 1, wherein said dose of IL-12 is less than about 3 μg/m2, between about 300 ng/m2 and about 2400 ng/m2, or between about 600 ng/m2 and about 1200 ng/m2.

12. The method of claim 11, wherein IL-12 is administered along with a carrier molecule that reduces the amount of IL-12 lost during administration.

13. The method of claim 12, wherein the carrier molecule is a protein at a concentration of about 5 times the concentration of IL-12.

14. The method of claim 1, wherein said intermediate dose of IL-12 is between a range of about 20 μg/m2 and about 75 μg/m2, or between about 22.5 μg/m2 and about 52.5 μg/m2.

15. The method of claim 1, wherein at least two doses of IL-12 are administered to said subject, wherein the first dose of IL-12 is less than about 100 μg/m2 and is administered within about 24 hours following an acute exposure to non-therapeutic whole body ionizing radiation, and the second dose of IL-12 is less than about 100 μg/m2 and is administered within about 96 hours following said acute exposure to non-therapeutic whole body ionizing radiation.

16. The method of claim 15, wherein said second dose is administered at least about 24 hours after said first dose.

17. The method of claim 15, wherein said second dose is less than said first dose.

18. The method of claim 15, wherein the second dose of IL-12 is administered at least about 72 hours after exposure.

19. The method of claim 1, wherein the IL-12 is rhuIL-12.

20. The method of claim 1, wherein the probability of survival of the subject is increased by at least 20%.

21. The method of claim 1, wherein said acute exposure is 8 Gy or less.

22. The method of claim 1, wherein the probability of survival of the subject is increased by at least 30%.

23. The method of claim 1, wherein the probability of survival of the subject is increased by at least 40%.

24. The method of claim 1, wherein the probability of survival of the subject is increased by at least 50%.

25. The method of claim 1, further comprising administering fluids, one or more antibiotics, blood or blood component transfusions, one or more growth factors or hematopoietic growth factors, or a combination thereof to the subject.

26. The method of claim 1, further comprising administering an effective dose of erythropoietin to the subject.

* * * * *